United States Patent
Shin et al.

(10) Patent No.: US 11,663,719 B2
(45) Date of Patent: May 30, 2023

(54) METHOD FOR HOSPITAL VISIT GUIDANCE FOR MEDICAL TREATMENT FOR ACTIVE THYROID EYE DISEASE, AND SYSTEM FOR PERFORMING SAME

(71) Applicant: THYROSCOPE INC., Ulsan (KR)

(72) Inventors: Kyubo Shin, Ulsan (KR); Jaemin Park, Busan (KR); Jongchan Kim, Ulsan (KR)

(73) Assignee: THYROSCOPE INC., Ulsan (KR)

( * ) Notice: Subject to any disclaimer, the term of this patent is extended or adjusted under 35 U.S.C. 154(b) by 0 days.

(21) Appl. No.: 17/939,040

(22) Filed: Sep. 7, 2022

(65) Prior Publication Data

US 2023/0005144 A1    Jan. 5, 2023

Related U.S. Application Data

(63) Continuation of application No. PCT/KR2022/009356, filed on Jun. 29, 2022.

(30) Foreign Application Priority Data

Jun. 30, 2021  (KR) .......................... 10-2021-0085542
Jun. 29, 2022  (KR) .......................... 10-2022-0079770

(51) Int. Cl.
*G06T 7/00*  (2017.01)
*G06T 7/70*  (2017.01)
(Continued)

(52) U.S. Cl.
CPC .............. *G06T 7/0012* (2013.01); *A61B 3/14* (2013.01); *A61B 5/4227* (2013.01); *A61B 5/445* (2013.01);
(Continued)

(58) Field of Classification Search
CPC ........... G06T 7/0012; G06T 7/12; G06T 7/70; G06T 2207/20021; G06T 2207/20132;
(Continued)

(56) References Cited

U.S. PATENT DOCUMENTS

2019/0370959 A1   12/2019   Krishna et al.
2020/0297206 A1    9/2020   Zakharov et al.
(Continued)

FOREIGN PATENT DOCUMENTS

CN    109543728 A    3/2019
CN    110246158 A    9/2019
(Continued)

OTHER PUBLICATIONS

Notice of Allowance of KR 10-2021-0085542 dated Dec. 22, 2021.
(Continued)

*Primary Examiner* — Nay A Maung
*Assistant Examiner* — Jose M Torres
(74) *Attorney, Agent, or Firm* — Dinsmore & Shohl LLP; Yongsok Choi, Esq.

(57) ABSTRACT

According to the present application, a computer-implemented method of predicting thyroid eye disease is disclosed. The method comprising: preparing a conjunctival hyperemia prediction model, a conjunctival edema prediction model, a lacrimal edema prediction model, an eyelid redness prediction model, and an eyelid edema prediction model, obtaining a facial image of an object, obtaining a first processed image and a second processed image from the facial image, wherein the first processed image is different from the second processed image, obtaining predicted values for each of a conjunctival hyperemia, a conjunctival edema and a lacrimal edema by applying the first processed image to the conjunctival hyperemia prediction model, the conjunctival edema prediction model, and the lacrimal
(Continued)

edema prediction model, and obtaining predicted values for each of an eyelid redness and an eyelid edema by applying the second processed image to the eyelid redness prediction model and the eyelid edema prediction model.

10 Claims, 29 Drawing Sheets

(51) Int. Cl.
  *G06T 7/12*   (2017.01)
  *A61B 5/00*   (2006.01)
  *A61B 3/14*   (2006.01)
  *G16H 50/20*  (2018.01)
(52) U.S. Cl.
  CPC .......... *A61B 5/4824* (2013.01); *A61B 5/4878* (2013.01); *G06T 7/12* (2017.01); *G06T 7/70* (2017.01); *G16H 50/20* (2018.01); *G06T 2207/20021* (2013.01); *G06T 2207/20132* (2013.01); *G06T 2207/30041* (2013.01); *G06T 2207/30201* (2013.01)
(58) Field of Classification Search
  CPC . G06T 2207/30041; G06T 2207/30201; A61B 3/14; A61B 5/4227; A61B 5/445; A61B 5/4824; A61B 5/4878; G16H 50/20
  See application file for complete search history.

(56) References Cited

U.S. PATENT DOCUMENTS

| | | | | |
|---|---|---|---|---|
| 2021/0007606 | A1* | 1/2021 | Su | ................ A61B 5/7278 |
| 2022/0142484 | A1 | 5/2022 | DiMaio et al. | |
| 2022/0313077 | A1* | 10/2022 | Singh | ................ A61B 3/14 |

FOREIGN PATENT DOCUMENTS

| | | |
|---|---|---|
| CN | 111839455 A | 10/2020 |
| JP | 2016032587 A | 3/2016 |
| JP | 2017503276 A | 1/2017 |
| JP | 2018099174 A | 6/2018 |
| KR | 1020080105723 A | 12/2008 |
| KR | 1020140089132 A | 7/2014 |
| KR | 1020140105313 A | 9/2014 |
| KR | 1020140108417 A | 9/2014 |
| KR | 1020150107565 A | 9/2015 |
| KR | 1020190082149 A | 7/2019 |
| KR | 102047237 B1 | 12/2019 |
| KR | 102058883 B1 | 12/2019 |
| KR | 1020200005060 A | 1/2020 |
| KR | 1020200077461 A | 6/2020 |
| KR | 1020200108993 A | 9/2020 |
| KR | 1020200133923 A | 12/2020 |
| KR | 1020210004695 A | 1/2021 |
| KR | 102223478 B1 | 3/2021 |
| KR | 1020210026597 A | 3/2021 |
| KR | 102347551 B1 | 1/2022 |
| KR | 102379061 B1 | 4/2022 |
| WO | 2020023959 A1 | 1/2020 |
| WO | WO-2022094446 A1 * | 5/2022 |

OTHER PUBLICATIONS

Office Action of KR 10-2021-0085542 dated Aug. 20, 2021.
Notice of Allowance of KR 10-2022-0079770 dated Oct. 31, 2022.
International Search Report and Written Opinion of PCT/KR2022/009452 dated Oct. 13, 2022.
International Search Report and Written Opinion of PCT/KR2022/009259 dated Oct. 6, 2022.
International Search Report and Written Opinion of PCT/KR2022/009356 dated Oct. 6, 2022.
Office Action of KR 10-2022-0080423 dated Sep. 20, 2022.
Non-Final Office Action of U.S. Appl. No. 17/945,270 dated Feb. 1, 2023.
Burns, Stephen A. et al., "Imaging the Retinal Vasculature", Annu Rev Vis Sci, vol. 7, pp. 129-153, HHS Public Access in PMC, Mar. 15, 2022.
Fondi, Klemens et al., "Evaluation of flicker induced hyperemia in the retina and optic nerve head measured by Laser Speckle Flowgraphy", Journal in PLoS One, vol. 13, No. 11, pp. 1-13, Nov. 28, 2018.
Kur, Joanna et al., "Cellular and physiological mechanisms underlying blood flow regulation in the retina and choroid in health and disease", Journal of Progress in Retinal and Eye Research, vol. 31, No. 5, pp. 377-406, May 3, 2012.

* cited by examiner

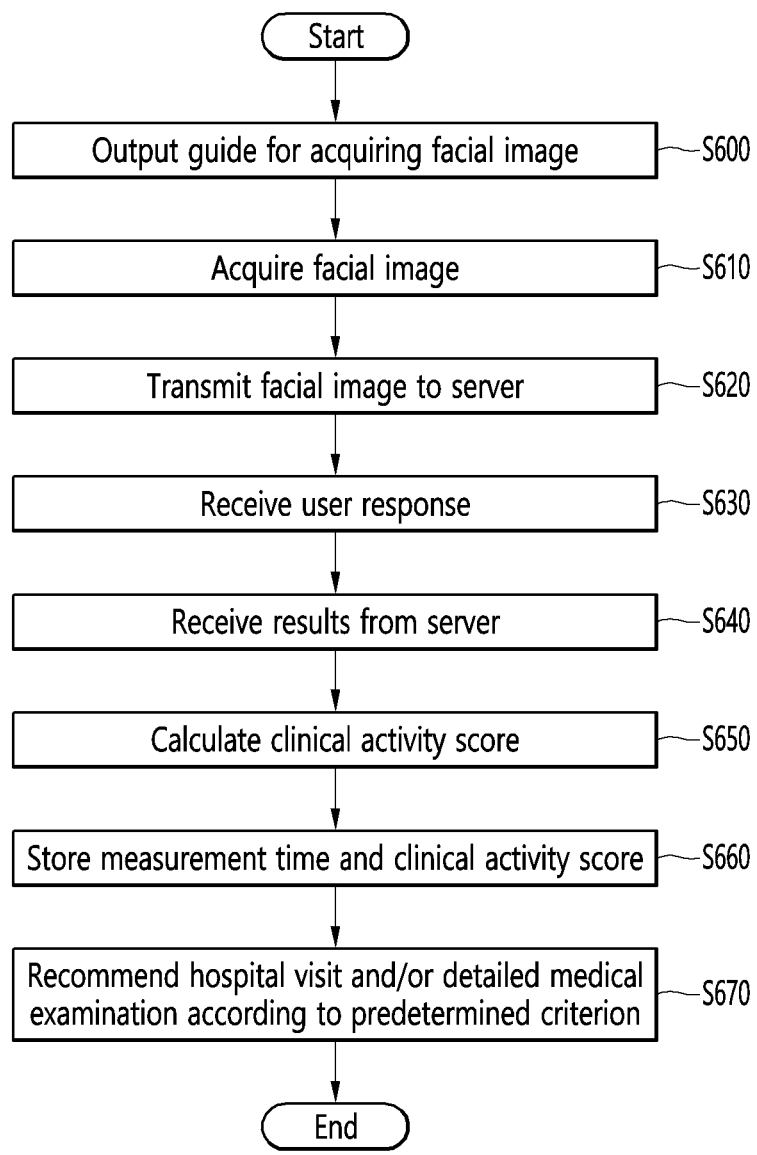

METHOD FOR HOSPITAL VISIT GUIDANCE FOR MEDICAL TREATMENT FOR ACTIVE THYROID EYE DISEASE, AND SYSTEM FOR PERFORMING SAME

CROSS-REFERENCE TO RELATED APPLICATIONS

This application is a continuation of International Application No. PCT/KR2022/009356 filed on Jun. 29, 2022, which claims priority to Korean Patent Application No. 10-2021-0085542 filed on Jun. 30, 2021 and Korean Patent Application No. 10-2022-0079770 filed on Jun. 29, 2022, the entire contents of which are herein incorporated by reference.

TECHNICAL FIELD

The present disclosure relates to a method for hospital visit guidance for medical treatment for active thyroid eye disease, and a system for performing the method.

BACKGROUND ART

An eye disease is a disease that occurs in the eyeball and surrounding parts. Many people in the world have been affected with eye diseases, and in severe cases, eye diseases cause great inconvenience in life, such as damage to eyesight, so it is necessary to monitor the occurrence or extent of the eye diseases.

In the meantime, an eye disease may be one of several complications caused by other diseases. For example, thyroid eye disease is a complication caused by thyroid dysfunction.

When thyroid eye disease becomes worse, the eyeball protrudes and cannot be treated without surgery. Therefore, early diagnosis of thyroid eye disease is very important for the treatment of thyroid eye disease. However, it is difficult to diagnose thyroid eye disease early because the disease does not show clear prognostic symptoms. In the medical community, efforts have been made to diagnose thyroid eye disease early through an evaluation method with the clinical activity score (CAS), which was proposed in 1989.

In determining the clinical activity score for thyroid eye disease, a total of seven items are considered, and the seven items are 1) spontaneous retrobulbar pain, 2) pain on an attempted upward or downward gaze, 3) redness of an eyelid, 4) redness of a conjunctiva, 5) swelling of an eyelid, 6) swelling of a conjunctiva, and 7) swelling of a lacrimal caruncle.

In order to determine a clinical activity score, it is essential that an individual visits a hospital or clinic in person and the doctor performs a medical examination through interview and observation with the naked eye. For example, spontaneous retrobulbar pain and pain on an attempted upward or downward gaze can be checked through interview by a doctor, and redness of an eyelid, redness of a conjunctiva, swelling of an eyelid, swelling of a conjunctiva, and swelling of a lacrimal caruncle can be checked by a doctor's observation with the naked eye. The doctor's medical examination with the naked eye and interview method for determining a clinical activity score require a hospital visit by a patient in person for a diagnosis of thyroid eye disease, as a precondition, so it is difficult to diagnose thyroid eye disease early.

Accordingly, it is desired to develop a method of enabling individuals to recognize a risk of eye disease more easily and quickly without a hospital visit in person so that continuous monitoring can be performed, and of informing a patient of a risk of eye disease to induce the patient to visit the hospital when necessary.

DISCLOSURE

Technical Problem

The disclosure in the present application is directed to providing a learning model used in predicting a clinical activity score for thyroid eye disease by using an image that is obtained with a digital camera that ordinary people can use rather than a professional medical diagnostic device.

In addition, the disclosure in the present application is directed to providing a method and a system for enabling ordinary people to continuously monitor a clinical activity score for thyroid eye disease without a doctor's help and a hospital visit in person.

In addition, the disclosure in the present application is directed to providing a method of recommending a hospital visit for medical treatment for active thyroid eye disease according to a result of monitoring a clinical activity score, and a system for performing the method.

Technical problems to be solved by the present application are not limited to the aforementioned technical problems and other technical problems which are not mentioned will be clearly understood by those skilled in the art from the present specification and the accompanying drawings.

Technical Solution

According to one aspect of the present application, a computer-implemented method of predicting thyroid eye disease is disclosed. The method comprising: preparing a conjunctival hyperemia prediction model, a conjunctival edema prediction model, a lacrimal edema prediction model, an eyelid redness prediction model, and an eyelid edema prediction model, obtaining a facial image of an object, obtaining a first processed image and a second processed image from the facial image, wherein the first processed image is different from the second processed image, obtaining predicted values for each of a conjunctival hyperemia, a conjunctival edema and a lacrimal edema by applying the first processed image to the conjunctival hyperemia prediction model, the conjunctival edema prediction model, and the lacrimal edema prediction model, obtaining predicted values for each of an eyelid redness and an eyelid edema by applying the second processed image to the eyelid redness prediction model and the eyelid edema prediction model, and determining a possibility of the object having thyroid eye disease based on the predicted values for the conjunctival hyperemia, the conjunctival edema, the lacrimal edema, the eyelid redness, and the eyelid edema. Wherein the first processed image is an image masked a region corresponding an inner of an outline of an iris and a region corresponding an outer of an outline of an eye and cropped along a first region comprising the outline of the eye based on position information of pixels corresponding the outline of the iris comprised in the eye and position information of pixels corresponding the outline of the eye, and wherein the second processed image is an image cropped along a second region that is wider than the first region based on position information of pixels corresponding the outline of the iris comprised in the eye and position information of pixels corresponding the outline of the eye.

In some embodiments, wherein the position information of pixels corresponding the outline of the iris comprised in the eye and the position information of pixels corresponding the outline of the eye are obtained by segmentation model.

In some embodiments, wherein the first processed image comprises a first processed left eye image and a first processed right eye image, and wherein the second processed image comprises a second processed left eye image and a second processed right eye image.

In some embodiments, wherein the conjunctival hyperemia prediction model comprises a left eye conjunctival hyperemia prediction model and a right eye conjunctival hyperemia prediction model, wherein the conjunctival edema prediction model comprises a left eye conjunctival edema prediction model and a right eye conjunctival edema prediction model, wherein the lacrimal edema prediction model comprises a left eye lacrimal edema prediction model and a right eye lacrimal edema prediction model, wherein the eyelid redness prediction model comprises a left eyelid redness prediction model and a right eye eyelid redness prediction model, and wherein the eyelid edema prediction model comprises a left eye eyelid edema prediction model and a right eye eyelid edema prediction model.

In some embodiments, wherein the predicted value for the conjunctival hyperemia is determined based on a result obtained by inputting the first processed left eye image to the left eye conjunctival hyperemia prediction model and a result obtained by inputting the first processed right eye image to the right eye conjunctival hyperemia prediction model, wherein the predicted value for the conjunctival edema is determined based on a result obtained by inputting the first processed left eye image to the left eye conjunctival edema prediction model and a result obtained by inputting the first processed right eye image to the right eye conjunctival edema prediction model, wherein the predicted value for the lacrimal edema is determined based on a result obtained by inputting the first processed left eye image to the left eye lacrimal edema prediction model and a result obtained by inputting the first processed right eye image to the right eye lacrimal edema prediction model, wherein the predicted value for the eyelid redness is determined based on a result obtained by inputting the second processed left eye image to the left eye eyelid redness prediction model and a result obtained by inputting the second processed right eye image to the right eye eyelid redness prediction model, and wherein the predicted value for the eyelid edema is determined based on a result obtained by inputting the second processed left eye image to the left eye eyelid edema prediction model and a result obtained by inputting the second processed right eye image to the right eye eyelid edema prediction model.

In some embodiments, the method further comprising: processing any one of the first processed left eye image and the first processed right eye image by inverting left and right, and processing any one of the second processed left eye image and the second processed right eye image by inverting left and right.

In some embodiments, wherein the predicted value for the conjunctival hyperemia is determined based on results obtained by inputting the image laterally inverted and by inputting the image not laterally inverted to the conjunctival hyperemia prediction model, wherein the predicted value for the conjunctival edema is determined based on results obtained by inputting the image laterally inverted and by inputting the image not laterally inverted to the conjunctival edema prediction model, wherein the predicted value for the lacrimal edema is determined based on results obtained by inputting the image laterally inverted and by inputting the image not laterally inverted to the lacrimal edema prediction model, wherein the predicted value for the eyelid redness is determined based on results obtained by inputting the image laterally inverted and by inputting the image not laterally inverted to the eyelid redness prediction model, and wherein the predicted value for the eyelid edema is determined based on results obtained by inputting the image laterally inverted and by inputting the image not laterally inverted to the eyelid edema prediction model.

In some embodiments, the method further comprising: resizing the first processed left eye image and the first processed right eye image, and resizing the second processed left eye image and the second processed right eye image.

Advantageous Effects

According to the disclosure in the present application, a clinical activity score for thyroid eye disease can be predicted using images obtained through a digital camera that ordinary people can use, rather than a professional medical diagnostic device.

In addition, according to the disclosure in the present application, ordinary people can continuously monitor a clinical activity score for thyroid eye disease without a doctor's help and a hospital visit in person, and a hospital visit is recommended when necessary.

DESCRIPTION OF DRAWINGS

FIG. 29 is a diagram illustrating a method of continuously monitoring a clinical activity score for thyroid eye disease, and a method of recommending a hospital visit on the basis of the former.

DETAILED DESCRIPTION

Figure 1:
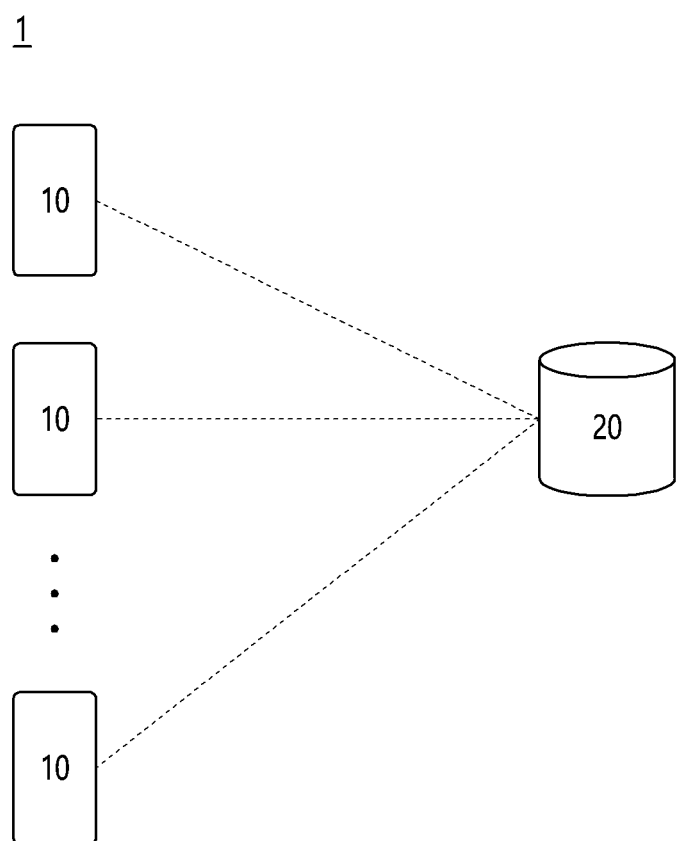
FIG. 1 is a diagram illustrating a system for predicting a clinical activity score for thyroid eye disease according to an embodiment described in the present application.

The above-described objectives, features, and advantages of the present application will be more apparent from the following detailed description with reference to the accompanying drawings. In addition, various modifications may be made to the present application, and various embodiments of the present application may be practiced. Therefore, specific embodiments will be described in detail below with reference to the accompanying drawings.

Throughout the specification, the same reference numerals denote the same elements in principle. In addition, elements having the same function within the same scope illustrated in the drawings of the embodiments are described using the same reference numerals, and a redundant description will be omitted.

A detailed description of a well-known function or configuration relating to the present application is omitted when determined as obfuscating the nature and gist of the present application. In addition, throughout the present specification, the terms first, second, and so on are used only to distinguish from one element to another.

In addition, the terms "module" and "part" that are used to name an element in the description below are used considering only the ease with which the present specification is written. The terms are not intended as having different special meanings or functions and thus may be used individually or interchangeably.

In the following embodiments, an expression used in the singular encompasses the expression of the plural, unless it has a clearly different meaning in the context.

In the following embodiments, it is to be understood that terms such as "including", "having", etc. are intended to indicate the existence of features or elements disclosed in the specification, and are not intended to preclude the possibility that one or more other features or elements may be added.

Sizes of elements in the drawings may be exaggerated or reduced for convenience of description. For example, any size and thickness of each element shown in the drawings are shown for convenience of description, and the present disclosure is not limited thereto.

In a case in which a particular embodiment is realized otherwise, a particular process may be performed out of the order described. For example, two processes described in succession may be performed substantially simultaneously, or may proceed in the order opposite to the order described.

In the following embodiments, when elements are referred to as being connected to each other, the elements are directly connected to each other or the elements are indirectly connected to each other with intervening elements therebetween. For example, in the present specification, when elements are referred to as being electrically connected to each other, the elements are directly electrically connected to each other or the elements are indirectly electrically connected with intervening elements therebetween.

According to one aspect of the present application, a computer-implemented method of predicting thyroid eye disease is disclosed. The method comprising: preparing a conjunctival hyperemia prediction model, a conjunctival edema prediction model, a lacrimal edema prediction model, an eyelid redness prediction model, and an eyelid edema prediction model, obtaining a facial image of an object, obtaining a first processed image and a second processed image from the facial image, wherein the first processed image is different from the second processed image, obtaining predicted values for each of a conjunctival hyperemia, a conjunctival edema and a lacrimal edema by applying the first processed image to the conjunctival hyperemia prediction model, the conjunctival edema prediction model, and the lacrimal edema prediction model, obtaining predicted values for each of an eyelid redness and an eyelid edema by applying the second processed image to the eyelid redness prediction model and the eyelid edema prediction model, and determining a possibility of the object having thyroid eye disease based on the predicted values for the conjunctival hyperemia, the conjunctival edema, the lacrimal edema, the eyelid redness, and the eyelid edema. Wherein the first processed image is an image masked a region corresponding an inner of an outline of an iris and a region corresponding an outer of an outline of an eye and cropped along a first region comprising the outline of the eye based on position information of pixels corresponding the outline of the iris comprised in the eye and position information of pixels corresponding the outline of the eye, and wherein the second processed image is an image cropped along a second region that is wider than the first region based on position information of pixels corresponding the outline of the iris comprised in the eye and position information of pixels corresponding the outline of the eye.

In some embodiments, wherein the position information of pixels corresponding the outline of the iris comprised in the eye and the position information of pixels corresponding the outline of the eye are obtained by segmentation model.

In some embodiments, wherein the first processed image comprises a first processed left eye image and a first processed right eye image, and wherein the second processed image comprises a second processed left eye image and a second processed right eye image.

In some embodiments, wherein the conjunctival hyperemia prediction model comprises a left eye conjunctival hyperemia prediction model and a right eye conjunctival hyperemia prediction model, wherein the conjunctival edema prediction model comprises a left eye conjunctival edema prediction model and a right eye conjunctival edema prediction model, wherein the lacrimal edema prediction model comprises a left eye lacrimal edema prediction model and a right eye lacrimal edema prediction model, wherein the eyelid redness prediction model comprises a left eyelid redness prediction model and a right eye eyelid redness prediction model, and wherein the eyelid edema prediction model comprises a left eye eyelid edema prediction model and a right eye eyelid edema prediction model.

In some embodiments, wherein the predicted value for the conjunctival hyperemia is determined based on a result obtained by inputting the first processed left eye image to the left eye conjunctival hyperemia prediction model and a result obtained by inputting the first processed right eye image to the right eye conjunctival hyperemia prediction model, wherein the predicted value for the conjunctival edema is determined based on a result obtained by inputting the first processed left eye image to the left eye conjunctival edema prediction model and a result obtained by inputting the first processed right eye image to the right eye conjunctival edema prediction model, wherein the predicted value for the lacrimal edema is determined based on a result obtained by inputting the first processed left eye image to the left eye lacrimal edema prediction model and a result obtained by inputting the first processed right eye image to the right eye lacrimal edema prediction model, wherein the predicted value for the eyelid redness is determined based on a result obtained by inputting the second processed left eye image to the left eye eyelid redness prediction model and a result obtained by inputting the second processed right eye image to the right eye eyelid redness prediction model, and wherein the predicted value for the eyelid edema is determined based on a result obtained by inputting the second processed left eye image to the left eye eyelid edema prediction model and a result obtained by inputting the second processed right eye image to the right eye eyelid edema prediction model.

In some embodiments, the method further comprising: processing any one of the first processed left eye image and the first processed right eye image by inverting left and right, and processing any one of the second processed left eye image and the second processed right eye image by inverting left and right.

In some embodiments, wherein the predicted value for the conjunctival hyperemia is determined based on results obtained by inputting the image laterally inverted and by inputting the image not laterally inverted to the conjunctival hyperemia prediction model, wherein the predicted value for the conjunctival edema is determined based on results obtained by inputting the image laterally inverted and by inputting the image not laterally inverted to the conjunctival edema prediction model, wherein the predicted value for the lacrimal edema is determined based on results obtained by inputting the image laterally inverted and by inputting the image not laterally inverted to the lacrimal edema prediction model, wherein the predicted value for the eyelid redness is determined based on results obtained by inputting the image laterally inverted and by inputting the image not laterally inverted to the eyelid redness prediction model, and wherein the predicted value for the eyelid edema is determined based on results obtained by inputting the image laterally inverted and by inputting the image not laterally inverted to the eyelid edema prediction model.

In some embodiments, the method further comprising: resizing the first processed left eye image and the first processed right eye image, and resizing the second processed left eye image and the second processed right eye image.

According to the present application, disclosed is a system for predicting a clinical activity score (CAS) for a user's thyroid eye disease, and for providing, on the basis of the CAS, guidance about the necessity for the user to visit the hospital.

1. Whole System (1) Hardware Construction of System

FIG. 1 is a diagram illustrating a system for predicting a clinical activity score for thyroid eye disease according to an embodiment described in the present application.

Referring to FIG. 1, the system 1 includes a plurality of user terminals 10 and a server 20.

Hereinafter, the plurality of user terminals 10 and the server 20 will be described in detail.

(2) Functions of User Terminals

The plurality of user terminals 10 transmit information to the server 20 over various networks, and receive information from the server 20.

The plurality of user terminals 10 obtain images of users' upper eyelids, lower eyelids, and eyeballs exposed to the outside by the upper eyelids and the lower eyelids (hereinafter, referred to as eye images). The plurality of user terminals 10 may perform necessary processing on the obtained eye images, or may transmit the obtained eye images or the processed eye images to the server 20.

The plurality of user terminals 10 may receive, from the server 20, prediction results about clinical activity scores processed by the server 20.

(3) Functions of Server

The server 20 transmits information to the plurality of user terminals 10 over various networks, and receive information from the plurality of user terminals 10.

The server 20 may receive the eye images from the plurality of user terminals 10. Herein, the server 20 may process the eye images. Alternatively, the server 20 may receive the processed eye images.

The server 20 may obtain, on the basis of the processed eye images, prediction results about clinical activity scores for users' thyroid eye diseases.

The server 20 may transmit the prediction results about the clinical activity scores to the plurality of user terminals 10.

(4) Software Construction of System

In order for the system 1 to operate, several software constructions are required.

To perform communication between the user terminals 10 and the server 20, terminal software needs to be installed on the plurality of user terminals 10, and server software needs to be installed on the server 20.

In order to perform pre-processing necessary for the eye images, various preprocessing algorithms may be used.

A plurality of learning models for predicting clinical activity scores on the basis of the preprocessed eye images may be used.

The plurality of preprocessing algorithms may be run by the terminal software installed on the user terminals 10, or may be run by the software installed on the server 20. Alternatively, some of the plurality of preprocessing algorithms may be executed by the user terminals 10, and the others may be executed by the server 20.

The plurality of learning models may be run by the software installed on the server 20. Alternatively, the plurality of learning models may be run by the terminal software installed on the user terminals 10. Alternatively, some of the plurality of learning models may be executed by the user terminals 10, and the others may be executed by the server 20.

(5) Elements of User Terminal

Figure 2:
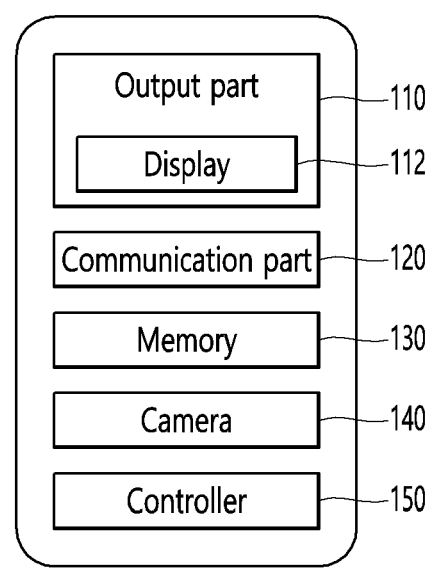
FIG. 2 is a block diagram illustrating a user terminal provided in the present application.

FIG. 2 is a block diagram illustrating a user terminal described in the present application.

Referring to FIG. 2, a user terminal 10 described in the present application includes an output part 110, a communication part 120, a memory 130, a camera 140, and a controller 150.

The output part 110 outputs various types of information according to control commands of the controller 150. According to an embodiment, the output part 110 may include a display 112 for outputting information visually to a user. Alternatively, although not shown in the drawings, a speaker for outputting information audibly to a user, and a vibration motor for outputting information tactually to a user may be included.

The communication part 120 may include a wireless communication module and/or a wired communication module. Herein, examples of the wireless communication module may include a Wi-Fi communication module, a cellular communication module, etc.

The memory 130 stores therein executable code readable by the controller 150, processed result values, necessary data, etc. Examples of the memory 130 may include a hard disk drive (HDD), a solid state disk (SSD), a silicon disk drive (SDD), ROM, RAM, etc. The memory 130 may store therein the above-described terminal software, and may store therein executable codes for realizing the above-described various preprocessing algorithms and/or learning models. Furthermore, the memory 130 may store therein an eye image obtained through the camera 140, the preprocessed eye images, etc.

The camera 140 is a digital camera, and may include an image sensor and an image processor. The image sensor is a device for converting an optical image into electrical signals, and may be provided as a chip in which multiple photodiodes are integrated. Examples of the image sensor may include a charge-coupled device (CCD), a complementary metal-oxide-semiconductor (CMOS), etc. In the meantime, the image processor may perform image processing on captured results, and may generate image information.

The controller 150 may include at least one processor. Herein, each of the processors may perform a predetermined operation by executing at least one instruction stored in the memory 130. Specifically, the controller 150 may process information according to the terminal software, the preprocessing algorithms, and/or the learning models running on the user terminal 10. In the meantime, the controller 150 controls the overall operation of the user terminal 10.

Although not shown in the drawings, the user terminal 10 may include a user input part. The user terminal 10 may receive, from a user, various types of information required for the operation of the user terminal 10 through the user input part.

(6) Elements of Server

Figure 3:
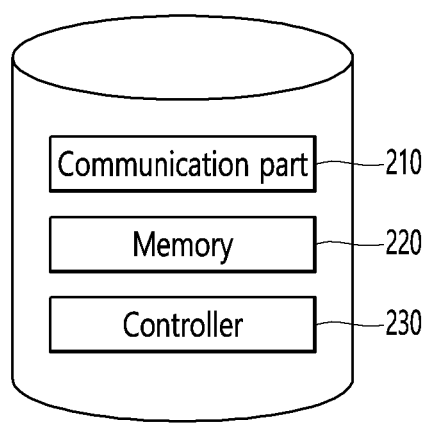
FIG. 3 is a block diagram illustrating a server described in the present application.

FIG. 3 is a block diagram illustrating a server described in the present application.

Referring to FIG. 3, the server 20 described in the present application includes a communication part 210, a memory 220, and a controller 230.

The communication part 210 may include a wireless communication module and/or a wired communication module. Herein, examples of the wireless communication module may include a Wi-Fi communication module, a cellular communication module, etc.

The memory 220 stores therein executable code readable by the controller 230, processed result values, necessary data, etc. Examples of the memory 220 may include a hard disk drive (HDD), a solid state disk (SSD), a silicon disk drive (SDD), ROM, RAM, etc. The memory 220 may store therein the above-described server software, and may store therein executable codes for realizing the above-described various preprocessing algorithms and/or learning models. Furthermore, the memory 220 may store therein an eye image received from the user terminal 10, the preprocessed eye images, etc.

The controller 230 may include at least one processor. Herein, each of the processors may perform a predetermined operation by executing at least one instruction stored in the memory 220. Specifically, the controller 230 may process information according to the server software, the preprocessing algorithms, and/or the learning models running on the server 20. In the meantime, the controller 230 controls the overall operation of the server 20.

Hereinafter, in order to more clearly and easily understand the technology described in the present application, an eye, an eyeball, and the tissues near the eyeball including an upper eyelid, a lower eyelid, and a lacrimal caruncle will be briefly described, and the terms related to an eye and the surroundings used in the present specification will be defined.

2. Construction of Eye and Definition of Terms (1) Eyeball and Surrounding Tissues FIG. 4 is a diagram illustrating an eye and the surrounding tissues that are exposed to the outside so that the eye and the surrounding tissues are captured by a camera when a picture of the face is taken using the camera.

Figure 4:
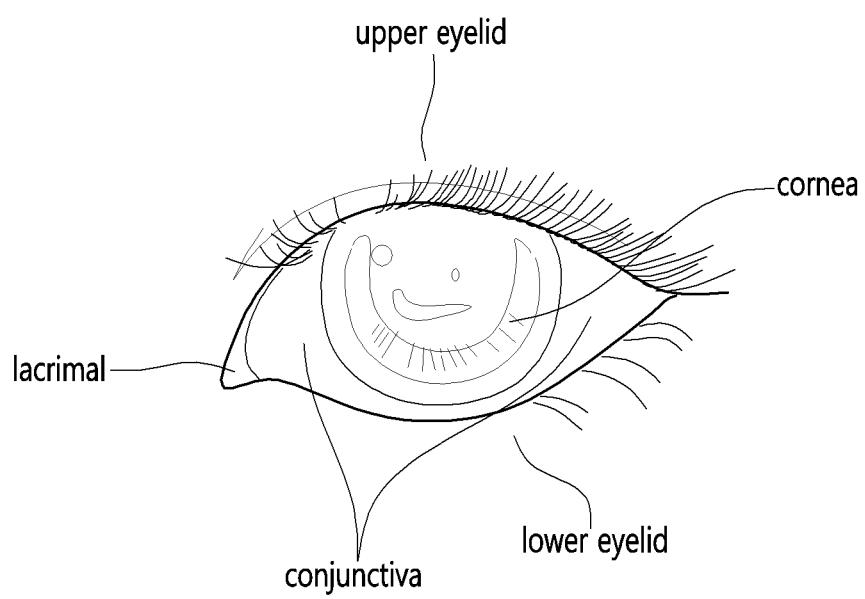
FIG. 4 is a diagram illustrating an eye and the surrounding tissues that are exposed to the outside so that the eye and the surrounding tissues are captured by a camera when a picture of the face is taken using the camera.

FIG. 4 shows eyelids (the upper eyelid and the lower eyelid), a lacrimal caruncle, and a conjunctiva and a cornea partially exposed and partially covered by the upper eyelid, the lower eyelid, and the lacrimal caruncle.

In general, an eye or eyeball is larger than that shown in FIG. 4. However, an eyeball is protected from the outside by tissues, such as the upper eyelid, and the lower eyelid, and thus, only part of the eyeball is exposed to the outside even when the person has his or her eye open.

(2) Definition of Terms

Conjunctiva, White of Eye

Hereinafter, a conjunctiva generally corresponds to the position of the white of an eye, so the terms the conjunctiva and the white of the eye may be used interchangeably.

Cornea, Iris

Hereinafter, a cornea generally corresponds to the position of the iris of an eye, so the terms cornea and iris may be used interchangeably. In the meantime, in the present specification, the term 'iris' is used in a sense including a pupil region.

Eyelids

Eyelids are two, upper and lower folds of skin covering the front part of an eyeball. Eyelids are also called palpebrae. The eyelid above an eyeball is called the upper eyelid, and the eyelid below the eyeball is called the lower eyelid. The outer surface is skin and the inner surface is a conjunctiva, and therebetween, there are muscles moving the eyelids, and tarsal plates containing meibomian glands, which are sebaceous glands, thus maintaining the shape of the eyelids. The eyelids protect the eyeball, and simultaneously, make the eyeball clean with tears by blinking the eye or make the cornea shiny and transparent.

Eyebrow

An eyebrow refers to hairs grown in an arc along the bony ridge above an eye.

Eyelashes

Eyelashes refer to hairs about 10 mm in length on the edge of upper and lower eyelids.

Eyeball Exposed to Outside

Figure 5:
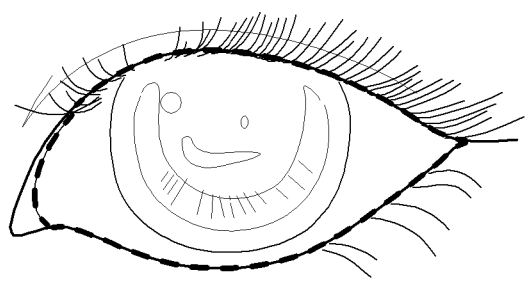
FIG. 5 is a diagram illustrating an eyeball exposed to the outside.

Hereinafter, "the eyeball exposed to the outside" means the part not covered by the upper eyelid, the lower eyelid, and the lacrimal caruncle, that is, the part exposed to the outside by the upper eyelid, the lower eyelid, and the lacrimal caruncle when a person has his or her eye open. For example, the inside of the dotted line shown in FIG. 5 is called "the eyeball exposed to the outside".

Outline of Eye

Figure 6:
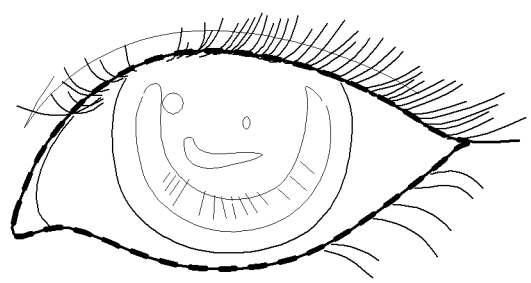
FIG. 6 is a diagram illustrating an outline of an eye.

Hereinafter, "the outline of the eye" means the outline of the part including both the eyeball exposed to the outside and the lacrimal caruncle region when a person has his or her eye open. That is, the outline of the region that is a combination of the eyeball exposed to the outside and the lacrimal caruncle is called "the outline of the eye". For example, the dotted line shown in FIG. 6 is called "the outline of the eye".

Cornea Exposed to Outside (Iris Exposed to Outside)

Figure 7:
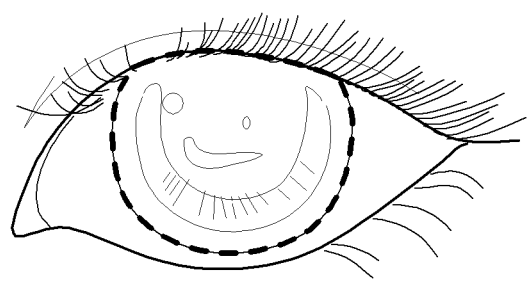
FIG. 7 is a diagram illustrating a cornea exposed to the outside.

Hereinafter, "the cornea exposed to the outside" means the cornea part not covered by the upper eyelid and the lower eyelid, that is, the cornea part exposed to the outside by the upper eyelid and the lower eyelid, when a person has his or her eye open. For example, the inside of the dotted line shown in FIG. 7 is called "the cornea exposed to the outside".

Conjunctiva Exposed to Outside (White of Eye Exposed to Outside)

Figure 8:
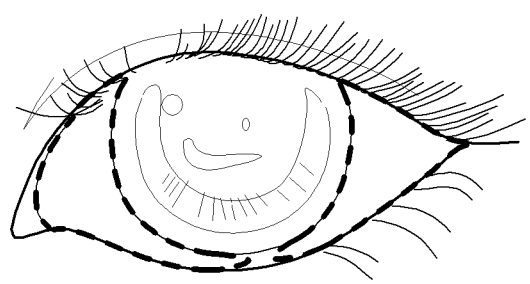
FIG. 8 is a diagram illustrating a conjunctiva exposed to the outside.

Hereinafter, "the conjunctiva exposed to the outside" means the conjunctiva part not covered by the upper eyelid, the lower eyelid, and the lacrimal caruncle, that is, the conjunctiva part exposed to the outside by the upper eyelid, the lower eyelid, and the lacrimal caruncle, when a person has his or her eye open. For example, the inside of the dotted line shown in FIG. 8 is called "the conjunctiva exposed to the outside".

Hereinafter, various image preprocessing algorithms for performing image preprocessing described in the present application will be described.

3. Image Preprocessing Algorithms (1) Necessity of Image Preprocessing

The present application is directed to providing a learning model for predicting a clinical activity score for thyroid eye disease by using an image obtained by a digital camera that ordinary people can use, rather than a professional medical diagnostic device.

To this end, in predicting a clinical activity score for thyroid eye disease, images that can be easily obtained by ordinary people for eyeballs and the tissues near the eyeballs need to be used. For example, an image analysis uses a digital image obtained by a digital camera or a camera built in a smartphone that can be easily used by ordinary people rather than a digital image obtained by a specialized medical device used in a medical institution.

Under this environment, a digital image obtained by a user is difficult to be standardized, and in order to more accurately and quickly recognize a digital image obtained by a user, various types of preprocessing of the obtained image are required.

(2) First Cropping (Two-Eye Image Cropping)

An image used in predicting a clinical activity score for thyroid eye disease needs to include a left eye, a right eye, and the surrounding regions.

However, for a more quick and accurate analysis, it is more efficient to use, in an image analysis, an image of only two eyes and the surrounding regions not including several unnecessary regions (for example, the regions corresponding to the nose, the mouth, the forehead, etc.) (hereinafter, referred to as a two-eye image), rather than an image of the entire face (hereinafter, referred to as a facial image).

Therefore, it is necessary to cut out the image including two eyes (left eye/right eye) (hereinafter, referred to as a two-eye image) from the image of the entire face (hereinafter, referred to as a facial image) obtained by the user.

Figure 9A:
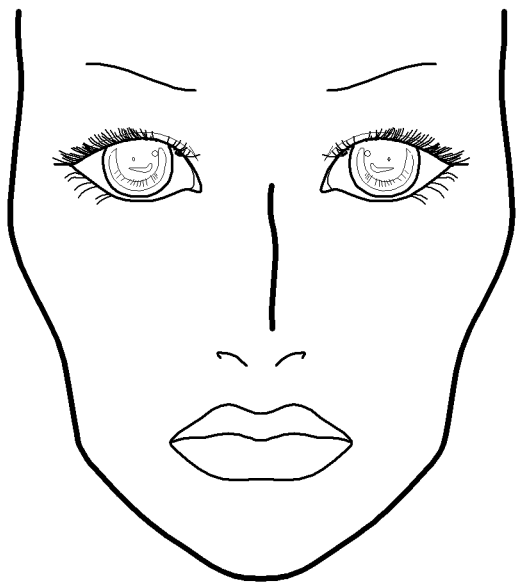
FIG. 9A is a diagram illustrating a facial image.
Figure 9B:
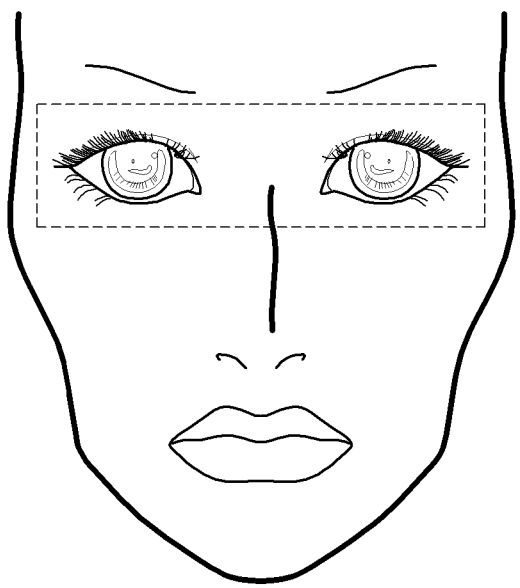
FIG. 9B is a diagram illustrating a two-eye image.

For example, from the facial image obtained by a user shown in FIG. 9(a), a two-eye image (the inner region of the quadrangle marked with the dotted line) as shown in FIG. 9(b) may be obtained. Hereinafter, obtaining a two-eye image from a facial image acquired by a user in this way is called two-eye image cropping or first cropping.

(3) Necessity of Applying Additional Cropping Methods

The inventors of the present application built a system for predicting scores for five items related to thyroid eye disease through prediction models, which will be described later, using a first cropped image (two-eye image) describe above, but it was found that the accuracy of prediction was low.

Figure 10A:
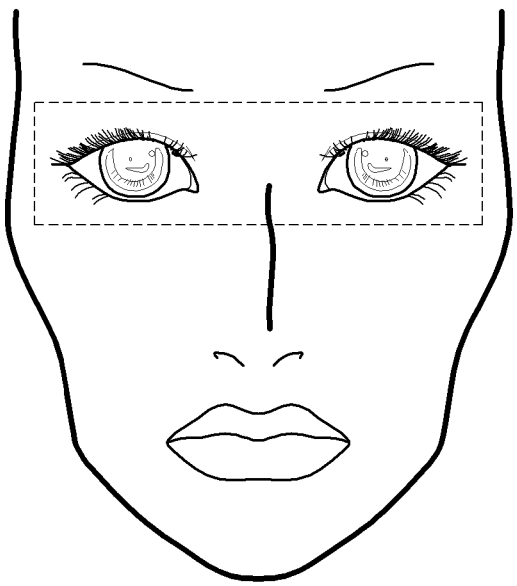
FIG. 10A is a diagram illustrating a two-eye image.
Figure 10B:
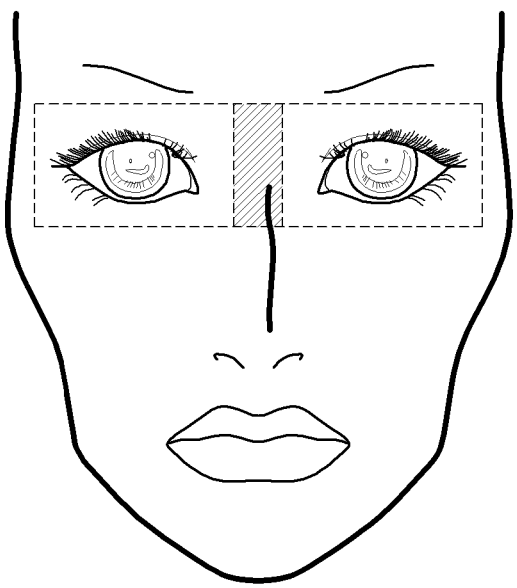
FIG. 10B is a diagram illustrating a left eye image and a right eye image.

The inventors of the present application determined that the accuracy of prediction was low because the two-eye image included many regions unnecessary for an analysis, and determined that it is necessary to obtain a more elaborate cropped image. That is, it was determined that it is more efficient to separately obtain and use the left eye image and the right eye image as shown in FIG. 10(b) than to use the two-eye image as shown in FIG. 10(a) in which the left eye and the right eye are included in one image.

(4) Necessity of Applying Different Cropping Methods

It has been described that five of the seven items for evaluating a clinical activity score for thyroid eye disease are the items evaluated according to a doctor's observation with the naked eye, of user's eyeballs and the surrounding regions. The five items are as follows.

1) Conjunctival hyperemia (redness of conjunctiva),
2) Conjunctival edema (swelling of conjunctiva),
3) Lacrimal edema (swelling of lacrimal caruncle),
4) Redness of eyelid, and
5) Eyelid edema (swelling of eyelid).

Hereinafter, as will be described later, in order to evaluate a clinical activity score for thyroid eye disease, independent prediction models provided in the present application have been applied to the five symptoms.

There may be a method of using an image to which different cropping methods are applied through five independent prediction models, but the inventors of the present application determined that sufficient prediction accuracy could be obtained by applying an image cropping method for analyzing a conjunctiva and a lacrimal caruncle and an image cropping method for analyzing an eyelid.

(5) Second Cropping (Eye-Outline-Based Cropping)

Hereinafter, eye-outline-based cropping (second cropping) will be described. Second cropping may be applied to both a right eye image and a left eye image, but a description will be given based on the case of obtaining a right eye cropped image for convenience.

Purpose of Second Cropping

Second cropping is to generate an image to be used as an input image of a model for predicting whether there is redness of a conjunctiva, a model for predicting whether there is swelling of a conjunctiva, and a model for predicting whether there is swelling of a lacrimal caruncle among the prediction models to be described later. Second cropping is to generate an image in which information on the cornea and the lacrimal caruncle is maximized and information on the other regions is minimized.

Input Image

Second cropping may be applied to a facial image or a two-eye image (first cropped image).

Detection of Outline of Eye

According to an embodiment, in order to detect the outline of the right eye, the pixels corresponding to the boundary between the upper eyelid and the eyeball and to the boundary between the lower eyelid and the eyeball may be detected. In addition, in order to detect the outline of the right eye, the pixels corresponding to the points at which the upper eyelid and the lower eyelid meet may be detected. Furthermore, in order to detect the outline of the right eye, the pixels corresponding to the lacrimal caruncle may be detected.

According to another embodiment, the outline pixels corresponding to the outermost part of the outline of the eye may be detected using an eye outline segmentation model, which will be described later.

Determination of Maximum Values and Minimum Values of X and Y Coordinates of Outline Pixels Determining the detected pixels, the maximum value $X_{max}$ of the X coordinate values, the minimum value $X_{min}$ of the X coordinate values, the maximum value $Y_{max}$ of the Y coordinate values, and the minimum value $Y_{min}$ of the Y coordinate values are determined.

Figure 11:
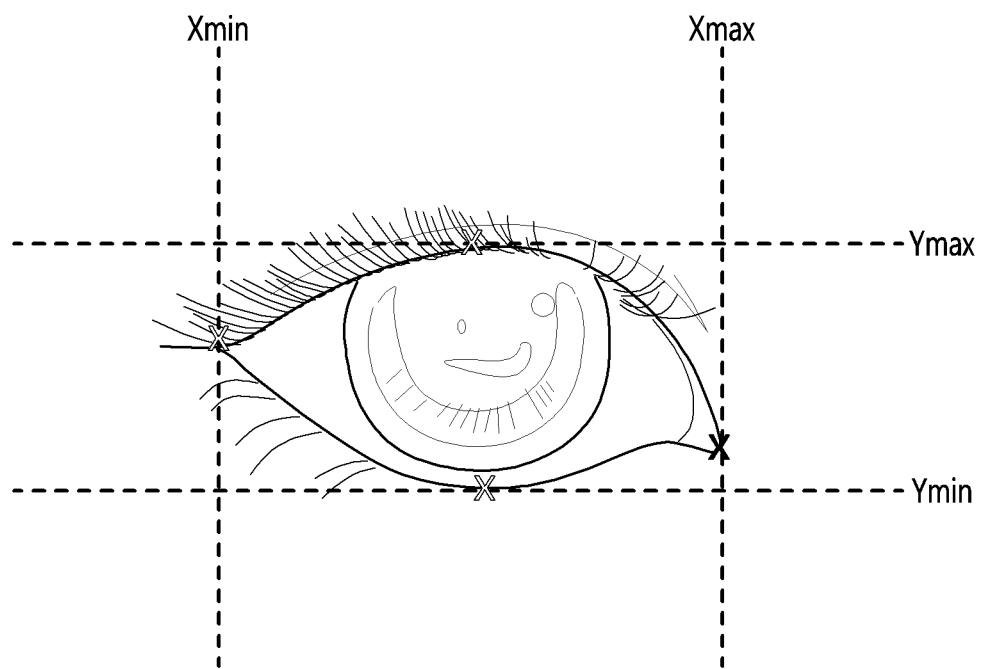
FIG. 11 is a diagram illustrating $X_{max}$, $X_{min}$, $Y_{max}$, and $Y_{min}$ of outline pixels.

FIG. 11 is a diagram illustrating $X_{max}$, $X_{min}$, $Y_{max}$, and $Y_{min}$ of outline pixels.

Cropped Region Determination

On the basis of the determined $X_{max}$, $X_{min}$, $Y_{max}$, and $Y_{min}$ of the outline pixels, a quadrangle having the following four points as vertexes is generated, and the region included inside the quadrangle is determined as a cropped region.

($X_{min}$, $Y_{max}$),
($X_{max}$, $Y_{max}$),
($X_{max}$, $Y_{min}$), and
($X_{min}$, $Y_{min}$)

Figure 12:
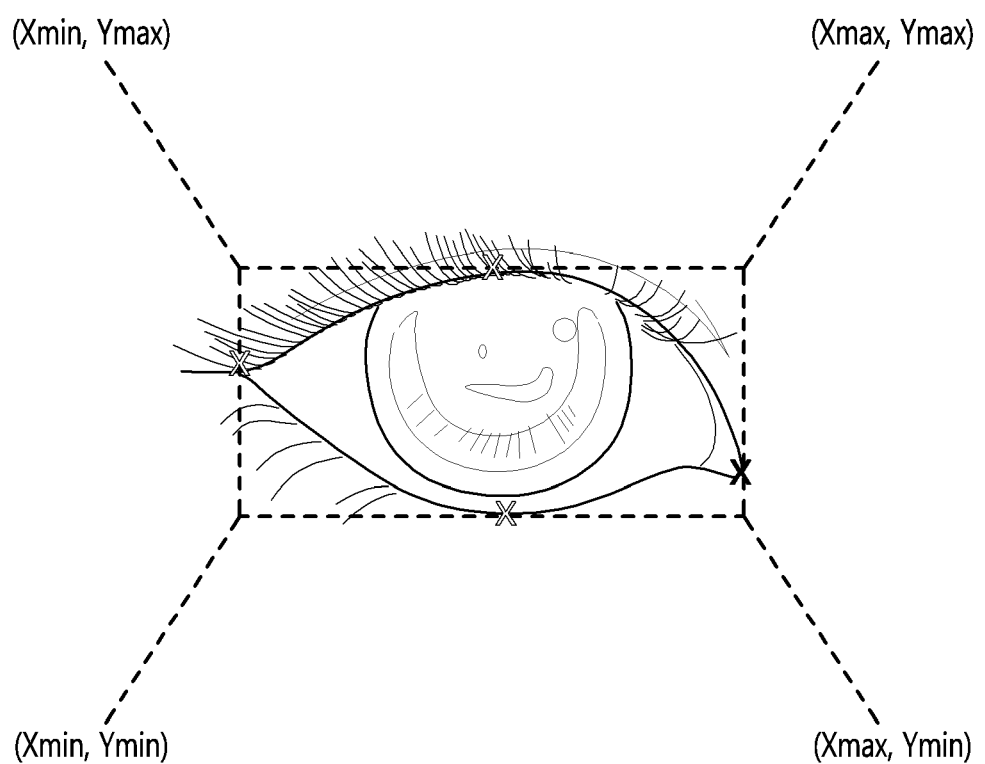
FIG. 12 is a diagram illustrating a second cropped region determined.

FIG. 12 is a diagram illustrating a second cropped region determined.

As described above, the second cropped region may be determined in the same manner for the left eye.

Generation of Second Cropped Images

Figure 13A:
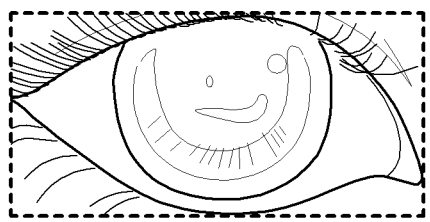
FIG. 13A is a diagram illustrating an example of a second cropped image.
Figure 13B:
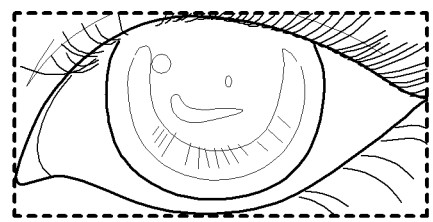
FIG. 13B is a diagram illustrating an example of a second cropped image.

The second cropped regions are determined, and on the basis of the determined second cropped regions, as shown in FIG. 13, second cropped images (a second right eye cropped image and a second left eye cropped image) may be generated from the facial image or the two-eye image by using the pixels included inside the second cropped regions determined as described above.

Hereinafter, the term "second right eye cropped image" and the term "right eye outline cropped image" may be used interchangeably, and the term "second left eye cropped image" and the term "left eye outline cropped image" may be used interchangeably.

In addition, without specific mention hereinbelow, the term "second cropped image (or outline cropped image)" may mean either a second right eye cropped image or a second left eye cropped image, or may mean both depending on the context.

A second cropped image means an image cropped with respect to 'the outline of the eye'. A cropped image generated in a method different from the above-described method is referred to as a second cropped image (outline cropped image) if the cropped image is generated such that the top, bottom, rightmost, and leftmost pixels of 'the outline of the eye' are included in the cropped region.

In the meantime, X coordinate values and Y coordinate values in the present application have different sizes and directions depending on a relative position with respect to a reference point, so the terms maximum value and minimum value should be understood in a relative sense, but not in an absolute sense. That is, as the position of the origin of the coordinate system is changed, the maximum value of the above-described X coordinate value may be the minimum value of the X coordinate value in the coordinate system of which the origin is changed, and the minimum value of the X coordinate value may be the maximum value of the X coordinate value in the coordinate system of which the origin is changed. This may be equally applied to the Y coordinate value.

(6) Third Cropping (Eyelid-Included Cropping)

Hereinafter, eyelid-included cropping (third cropping) will be described. Third cropping may be applied to both a right eye image and a left eye image, but a description will be given based on the case of obtaining a right eye cropped image for convenience.

Purpose of Third Cropping

Third cropping is to generate an image to be used as an input image of a model for predicting whether there is redness of eyelids and a model for predicting whether there is swelling of eyelids among the prediction models to be described later. Third cropping is to include information on eyelids in the image. Herein, rather than cropping with only the pixels corresponding to eyelids, it may be better to generate a cropped image such that all the pixels included in the outline of the eye are included. This is because inference and determination are required for color values in order to predict whether there is eyelid redness, and the color values of the pixels corresponding to the iris and/or the white of the eye may be used.

Input Image

Third cropping may be applied to a facial image or a two-eye image (first cropped image).

Detection of Outline of Eye, and Determination of Maximum Values and Minimum Values of X and Y Coordinates of Outline Pixels According to an embodiment, the eye outline detection method described in second cropping may be applied as it is, or the outline pixels corresponding to the outermost part of the outline of the eye may be detected. Determining the detected pixels, the maximum value $X_{max}$ of the X coordinate values, the minimum value $X_{min}$ of the X coordinate values, the maximum value $Y_{max}$ of the Y coordinate values, and the minimum value $Y_{min}$ of the Y coordinate values may be determined.

Cropped Region Determination #1

On the basis of the determined $Y_{max}$ value and $Y_{min}$ value, a first expansion value $Y_e$ determined according to a predetermined criterion is added to the $Y_{max}$ value, and a second expansion value $Y_e'$ determined according to a predetermined criterion is subtracted from the $Y_{min}$ value, and a third cropped region may be determined similarly to the above-described method of determining the second cropped region.

That is, a quadrangle having the following four points as vertexes is generated, and the region included inside the quadrangle is determined as a third cropped region.

($X_{min}$, $Y_{max}+Y_e$),
($X_{max}$, $Y_{max}+Y_e$),
($X_{max}$, $Y_{min}-Y_e'$) and
($X_{min}$, $Y_{min}-Y_e'$)

When the third cropped region is determined in this way, more pixels corresponding to the upper eyelid and the lower eyelid may be included in the image, compared to the second cropped region.

Herein, the first expansion value and the second expansion value may be the same, but are not necessarily the same.

In the meantime, the criterion for determining the first expansion value and the criterion for determining the second expansion value may be the same, but are not necessarily the same.

The first expansion value and the second expansion value may be determined on the basis of the size of the second cropped region. For example, the first expansion value and the second expansion value may be determined using the number of pixels corresponding to the length calculated by multiplying an expansion percentage by the horizontal length of the second cropped region. As another example, the first expansion value and the second expansion value may be determined using the number of pixels corresponding to the length calculated by multiplying an expansion percentage by the vertical length of the second cropped region.

Herein, the specific percentage may be any one of the following: 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 50, 51, 52, 53, 54, 55, 56, 57, 58, 59, and 60%.

The expansion percentage used in determining the first expansion value and the expansion percentage used in determining the second expansion value may be the same, but are not necessarily the same and may be different from each other.

When the horizontal length of the second cropped region is used in determining the first expansion value, the horizontal length may also be used in determining the second expansion value, but no limitation thereto is imposed and the vertical length may be used in determining the second expansion value.

Cropped Region Determination #2

On the basis of the determined $X_{max}$ value and $X_{min}$ value, a first width expansion value $X_{we}$ is determined according to a predetermined criterion, and a second width expansion value $X_{we}'$ is determined according to a predetermined criterion.

On the basis of the determined $Y_{max}$ value and $Y_{min}$ value, a first height expansion value $Y_{he}$ is determined according to a predetermined criterion, and a second height expansion value $Y_{he}'$ is determined according to a predetermined criterion.

On the basis of the value obtained by adding the first width expansion value $X_{we}$ to the $X_{max}$ value, the value obtained by subtracting the second width expansion value $X_{we}'$ from the $X_{min}$ value, the value obtained by adding the first height expansion value $Y_{he}$ to the $Y_{max}$ value, and the value obtained by subtracting the second height expansion value $Y_{he}'$ from the $Y_{min}$ value, a third cropped region may be determined similarly to the above-described method of determining the second cropped region.

That is, a quadrangle having the following four points as vertexes is generated, and the region included inside the quadrangle is determined as a third cropped region.

$(X_{min}-X_{we}', Y_{max}+Y_{he})$,
$(X_{max}+X_{we}, Y_{max}+Y_{he})$,
$(X_{max}+X_{we}, Y_{min}-Y_{he}')$ and
$(X_{min}-X_{we}', Y_{min}-Y_{he}')$ When the third cropped region is determined in this way, more pixels corresponding to the upper eyelid and the lower eyelid may be included in the image, compared to the second cropped region.

Furthermore, the cropped image includes more pixels in a left-right direction than the image cropped by the method "cropped region determination #1". As a result, the cropped image includes more information on the upper eyelid and the lower eyelid. Because the width of the upper eyelid and the lower eyelid is generally wider than the width of the eyeball exposed to the outside, more pixels corresponding to the upper eyelid and the lower eyelid are included through vertical expansion as well as horizontal expansion.

Herein, the first width expansion value and the second width expansion value may be the same, but are not necessarily the same.

In the meantime, the criterion for determining the first height expansion value and the criterion for determining the second height expansion value may be the same, but are not necessarily the same.

The first width expansion value and the second width expansion value may be determined on the basis of the size of the second cropped region. For example, the first width expansion value and the second width expansion value may be determined using the number of pixels corresponding to the length calculated by multiplying an expansion percentage by the horizontal length of the second cropped region. As another example, the first width expansion value and the second width expansion value may be determined using the number of pixels corresponding to the length calculated by multiplying an expansion percentage by the vertical length of the second cropped region.

Herein, the specific percentage may be any one of the following: 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 50, 51, 52, 53, 54, 55, 56, 57, 58, 59, and 60%.

The expansion percentage used in determining the first width expansion value and the expansion percentage used in determining the second width expansion value may be the same, but are not necessarily the same and may be different from each other.

When the horizontal length of the second cropped region is used in determining the first width expansion value, the horizontal length may also be used in determining the second width expansion value, but no limitation thereto is imposed and the vertical length may be used in determining the second expansion value.

In the meantime, the method of determining the first height expansion value and the second height expansion value is the same as the above-described method of determining the first expansion value and the second expansion value, so a detailed description will be omitted.

Generation of Third Cropped Images

The third cropped regions are determined, and on the basis of the determined third cropped regions, as shown in FIG. 14, third cropped images (a third right eye cropped image and a third left eye cropped image) may be generated from the facial image or the two-eye image by using the pixels included inside the second cropped regions determined as described above.

Figure 14A:
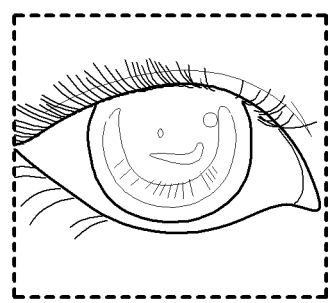
FIGS. 14A and 14B are diagrams illustrating examples of third cropped images.
Figure 14A:
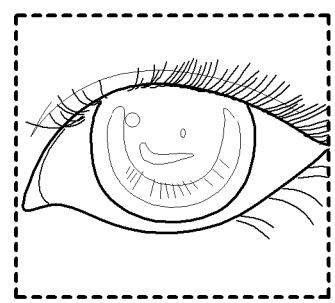
Figure 14B:
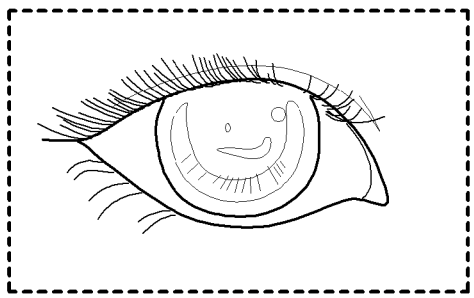
Figure 14B:
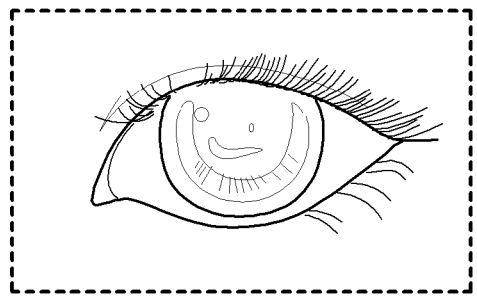

For reference, FIG. 14(a) shows the third cropped images cropped by the above-described method 'cropped region determination #1', and FIG. 14(b) shows the third cropped images cropped by the above-described method 'cropped region determination #2'.

Hereinafter, the term "third right eye cropped image" and the term "right eyelid-included-cropped image" may be used interchangeably, and the term "third left eye cropped image" and the term "left eyelid-included-cropped image" may be used interchangeably.

In addition, without specific mention hereinbelow, the term "third cropped image (or eyelid-included cropped image)" may mean either a third right eye cropped image or a third left eye cropped image, or may mean both depending on the context.

A third cropped image means an image that is generated such that the image includes information on eyelids. A cropped image generated in a method different from the above-described method is referred to as a third cropped image (eyelid-included cropped image) if the boundary of the cropped region is determined such that the pixels corresponding to eyelids are additionally included.

(7) Iris Segmentation

Hereinafter, iris segmentation will be described.

Iris segmentation may be performed by a model that distinguishes a region corresponding to the iris or cornea from an image of the eyeball and the surroundings.

Figure 15:
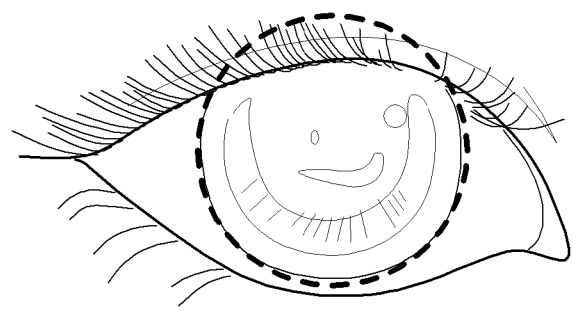
FIGS. 15 and 16 are diagrams illustrating iris segmentation.
Figure 15:
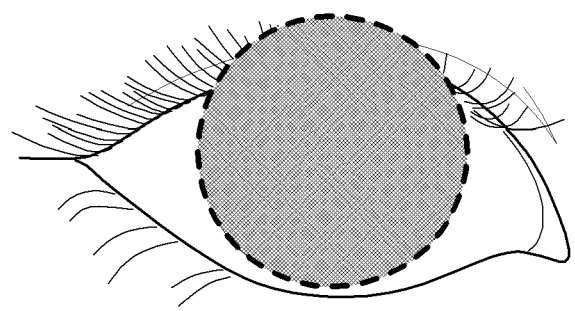

By using iris segmentation, the pixels corresponding to the iris within the image may be inferred as shown in FIG. 15.

Figure 16:
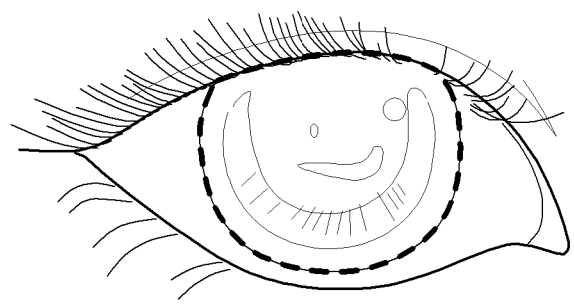
Figure 16:
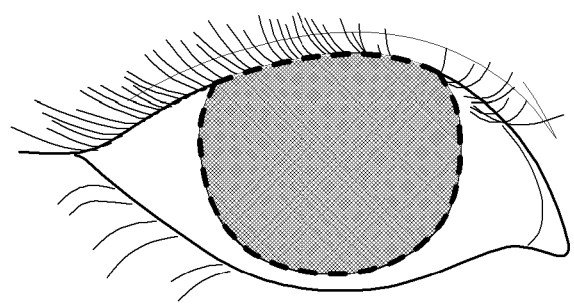

By using iris segmentation, the pixels corresponding to the iris exposed to the outside within the image may be inferred as shown in FIG. 16.

The model for iris segmentation may receive a facial image as input data, may output '1' for the pixels inferred to be the pixels corresponding to the iris within the facial image, and may output '0' for the other pixels.

The iris segmentation model may be trained using training data that includes a facial image and an image in which the pixel values of the pixels corresponding to the iris within a facial image are '1' and the pixel values of the remaining pixels are '0'.

Although it has been described that a facial image is received as input data and is subjected to iris segmentation, iris segmentation may also be performed using the above-described two-eye image as input data.

(8) Eye Outline Segmentation

Hereinafter, eye outline segmentation will be described.

Eye outline segmentation may be performed by a model that distinguishes a region corresponding to the inside of the outline of the eye from an image of the eyeball and the surroundings.

Figure 17:
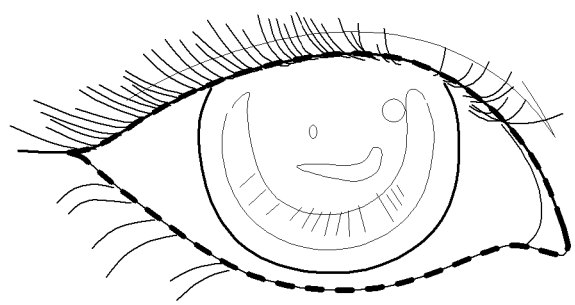
FIG. 17 is a diagram illustrating eye outline segmentation.
Figure 17:
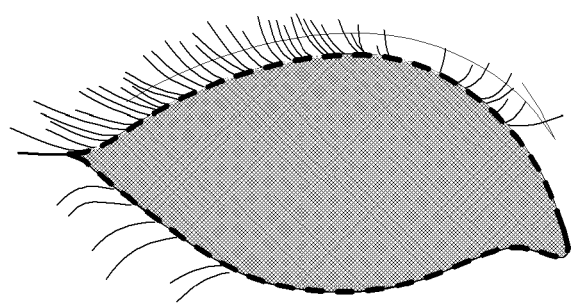

By using eye outline segmentation, the pixels corresponding to the inside of the outline of the eye within the image may be inferred as shown in FIG. 17.

The model for eye outline segmentation may receive a facial image as input data, may output '1' for the pixels inferred to be the pixels corresponding to the inside of the outline of the eye within the facial image, and may output '0' for the other pixels.

The eye outline segmentation model may be trained using training data that includes a facial image and an image in which the pixel values of the pixels corresponding to the inside of the outline of the eye within the facial image are '1' and the pixel values of the remaining pixels are '0'.

(9) Masking

First Masking

In the present application, first masking means that in an image, removed is information reflected in the pixel values corresponding to the regions excluding the pixels corresponding to the conjunctiva and the lacrimal caruncle.

Removing information reflected in pixel values means changing the pixel values of the pixels of which information is to be removed into a predetermined particular value. For example, all the pixel values of the pixels of which information is to be removed may be changed to 0.

First masking may be performed before an image is input to the models for predicting symptoms related to the conjunctiva and the lacrimal caruncle among the above-described prediction models for predicting a clinical activity score for thyroid eye disease.

Second Masking

In the present application, second masking means that in an image, removed is information reflected in the pixel values corresponding to the regions corresponding to the cornea exposed to the outside (the iris exposed to the outside).

Second masking may be performed before an image is input to the models for predicting symptoms related to eyelids (upper eyelid and lower eyelid) among the above-described prediction models for predicting a clinical activity score for thyroid eye disease.

Method of First Masking

First masking may be performed on a first masking target image that is one selected from the group of a facial image, a first cropped image (two-eye image), and a second cropped image (outline cropped image).

On the basis of the first masking target image, the eye outline segmentation result, and the iris segmentation result, a first masking image may be generated. For example, from the first masking target image, the values of the pixels excluding the pixels corresponding to the inside of the outside of the eye, and the pixels values of the pixels corresponding to the iris (or the iris exposed to the outside) may be removed.

Figure 18A:
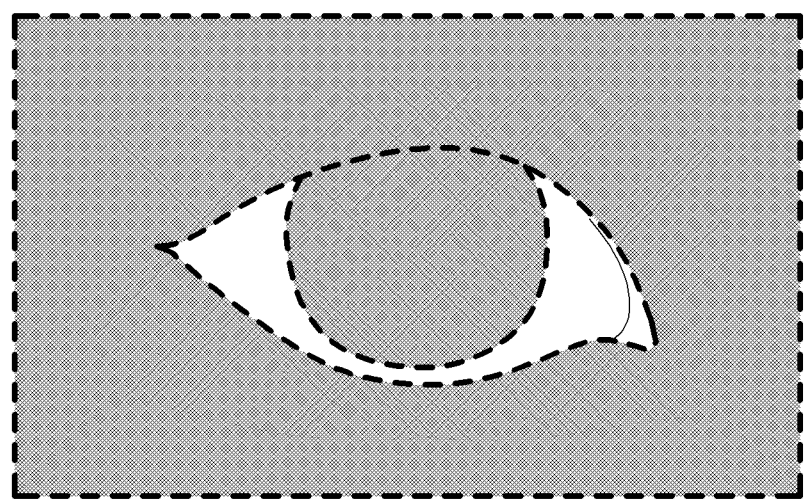
FIG. 18A is a diagram illustrating an example of a first masking image.
Figure 18B:
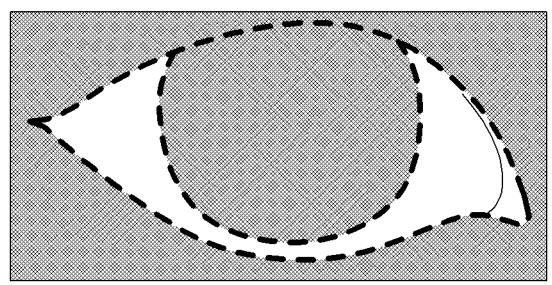
FIG. 18B is a diagram illustrating an example of a first masking image.

FIG. 18 is a diagram illustrating examples of a first masking image.

Method of Second Masking

Second masking may be performed on a second masking target image that is one selected from the group of a facial image, a first cropped image (two-eye image), and a third cropped image (eyelid-included cropped image).

On the basis of the second masking target image, the eye outline segmentation result, and the iris segmentation result, a second masking image may be generated. For example, from the second masking target image, the pixels values of the pixels corresponding to the inside of the outline of the eye and simultaneously corresponding to the iris (or the iris exposed to the outside) may be removed.

Figure 19:
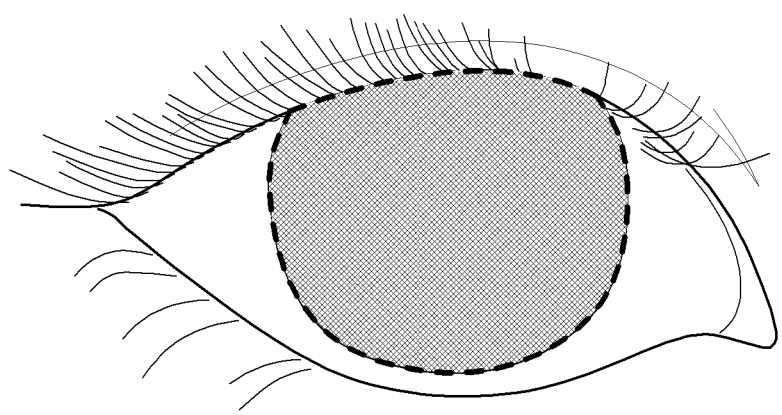
FIG. 19 is a diagram illustrating an example of a second masking image.

FIG. 19 is a diagram illustrating an example of a second masking image.

Another Embodiment of First Masking

According to the above description, it has been described that first masking removes all the pixel values of the pixels corresponding to the regions excluding the pixels corresponding to the conjunctiva and the lacrimal caruncle, but first masking may not remove the pixel values of the pixels corresponding to the cornea (iris) when necessary.

However, since colors of irises may vary according to race, removing the pixel values of the pixels corresponding to the iris is advantageous for quicker learning and higher accuracy.

Option of Second Masking

According to the above description, it has been described that second masking removes all the pixel values of the pixels corresponding to the iris, but it is allowed not to perform second masking at all.

However, since colors of irises may vary according to race, removing the pixel values of the pixels corresponding to the iris by performing second masking is advantageous for quicker learning and higher accuracy.

(10) Lateral Inversion

Necessity of Lateral Inversion

According to a method, which is provided in the present application, of predicting a clinical activity score for thyroid eye disease, cropped images of the left eye and the right eye are used instead of using a two-eye image.

In the meantime, the outline of an eye is asymmetric. For example, with respect to the right eye, the lacrimal caruncle is at the left end of the right eye, but the point at which the upper eyelid and the lower eyelid meet naturally is at the right end of the right eye.

Accordingly, for quicker learning and more accurate prediction, it is more effective to distinguish and use a learning model trained with respect to a right eye and a learning model trained with respect to a left eye.

However, when the left eye is turned over to be the right eye on the basis of the line of symmetry between the left eye and the right eye, the shape features of the right eye and the left eye are similar to each other.

Accordingly, according to the present application, either the right eye or the left eye is used without lateral inversion, the other eye is used with lateral inversion, so that only one learning model can be used.

Lateral Inversion Method

Laterally inverting an image (converting the left and the right of the image) means that with a left and right reference line (X=a) vertically crossing the image to be inverted and dividing the image in half left and right, when a first pixel value corresponds to the pixel (a+Δ, Y) in the image and a second pixel value corresponds to the pixel (a−Δ, Y), the pixel value of (a+Δ, Y) is changed from the first pixel value to the second pixel value and the pixel value of (a−Δ, Y) is changed from the second pixel value to the first pixel value.

Lateral Inversion Target Image

Laterally inverting either the image of the left eye or the image of the right eye is sufficient. Which one of the left eye image and the right eye image is subjected to lateral inversion is determined according to which one of the left eye image and the right eye image is based when the prediction models, which will be described later, are trained.

In the meantime, lateral inversion may be performed on the image on which both masking and cropping (second cropping or third cropping) have been performed, or lateral inversion may be performed on the image on which only cropping has been performed, but masking has not been performed.

Figure 20:
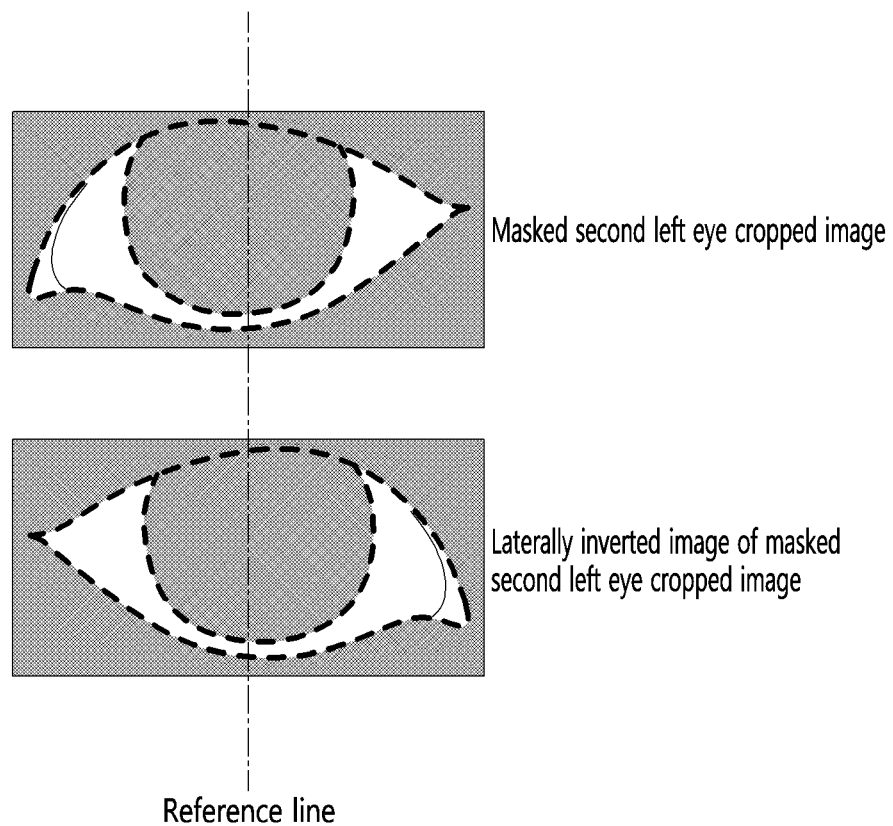
FIGS. 20 to 22 are diagrams illustrating various examples of original images and laterally inverted images.
Figure 21:
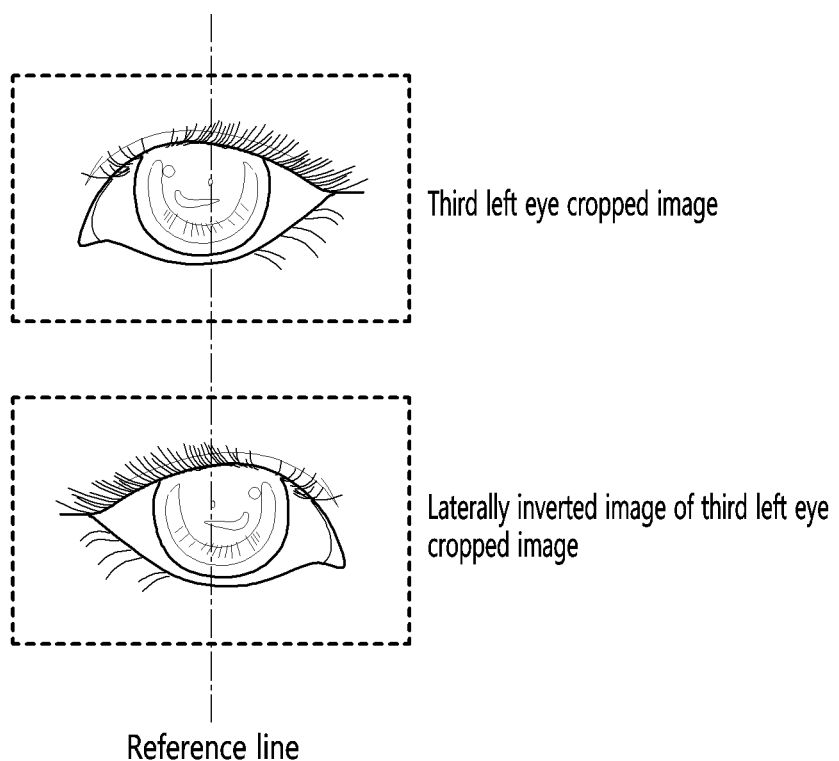
Figure 22:
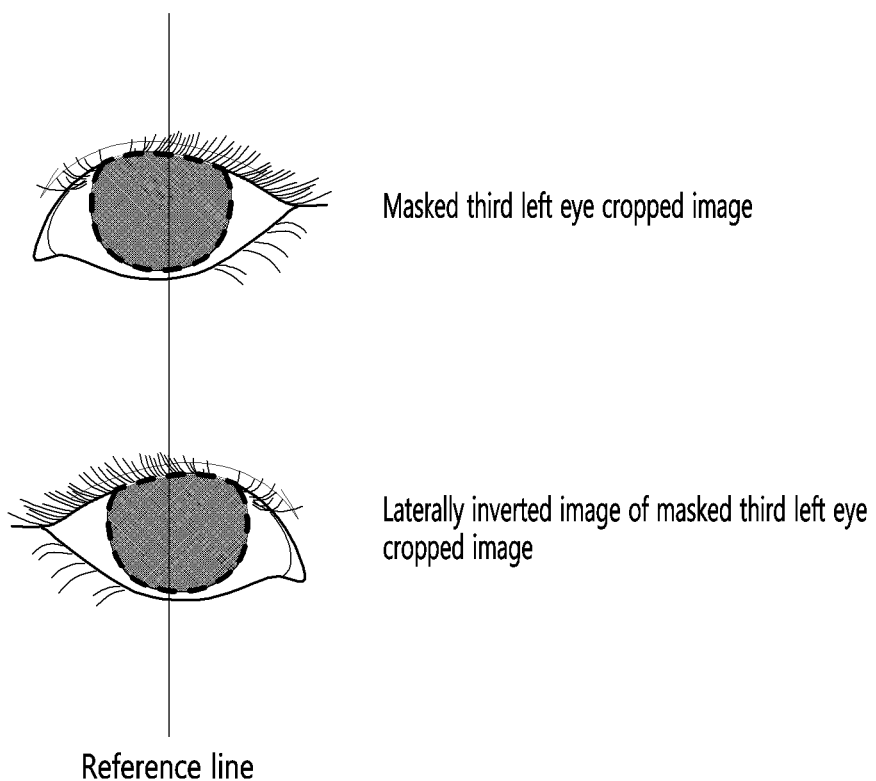

FIGS. 20 to 22 are diagrams illustrating various examples of original images and laterally inverted images.

Option of Lateral Inversion

However, as described above, lateral inversion is applied to unify a prediction model for the left eye and a prediction model for the right eye. Therefore, if the prediction model for the left eye and the prediction model for the right eye are realized as different models, lateral inversion preprocessing may be omitted.

(11) Resizing

Necessity of Resizing

As described above, when an image is cropped with respect to the outline of the eye and the cropped image is used, sizes of eyes vary from person to person and cropped images vary in size from person to person.

In the meantime, when a left eye image and a right eye image are independently cropped and obtained, the left eye cropped image and the right eye cropped image of the same person are different from each other because of the difference in size between the left eye and the right eye.

For this reason, before an eye image is input to the prediction models, which will be described later, it is necessary to resize the eye image to standard sizes corresponding to the respective prediction models.

Standard Size for each Prediction Model

The standard sizes corresponding to a first prediction model to a fifth prediction model, respectively, may be different from each other.

The standard sizes corresponding to the prediction models using a second cropped image as an input image may be the same.

The standard sizes corresponding to the prediction models using a third cropped image as an input image may be the same.

The standard size corresponding to the prediction models using a second cropped image as an input image may be different from the standard size corresponding to the prediction models using a third cropped image as an input image.

Alternatively, the standard sizes corresponding to the first prediction model to the fifth prediction model, respectively, may be the same.

Resizing Method

The size of a resizing target image is adjusted to a standard size.

When the width or height of the resizing target image is greater than the width or height of the standard size, the width or height of the resizing target image may be decreased.

When the width or height of the resizing target image is less than the width or height of the standard size, the width or height of the resizing target image may be increased.

In resizing, the aspect ratio of the image before resizing may be different from the aspect ratio of the image after resizing.

4. Prediction Models (1) First Prediction Model

Purpose and Operation of First Prediction Model

The first prediction model is a model for predicting whether there is conjunctival hyperemia.

The first prediction model may receive an eye image as input data and may output a probability value that the conjunctiva captured in the input eye image is hyperemic.

When the first prediction model includes a first left eye prediction model and a first right eye prediction model, the first left eye prediction model may receive a left eye image and output a probability value that the conjunctiva captured in the left eye image is hyperemic, and the first right eye prediction model may receive a right eye image and may output a probability value that the conjunctiva captured in the right eye image is hyperemic.

When the first prediction model is not dualized and is realized as one model, the first prediction model may receive either a right eye image or a left eye image to output a probability value that the conjunctiva captured in the input image is hyperemic, and may receive the other image to output a probability value that the conjunctiva captured in the input image is hyperemic.

The eye image may be an image preprocessed by the above-described preprocessing algorithms.

For example, the eye image may be an image on which preprocessing according to second cropping is performed.

As another example, the eye image may be an image on which preprocessing including second cropping and resizing is performed.

As still another example, the eye image may be an image on which preprocessing including second cropping, first masking, and resizing is performed.

As yet still another example, the eye image may be an image on which preprocessing including second cropping, first masking, lateral inversion, and resizing is performed.

In the present specification, the first prediction model may be called a conjunctival hyperemia prediction model.

Training of First Prediction Model

To train the first prediction model, a plurality of training data sets may be prepared. A training data set may include an eye image and an evaluation value for conjunctival hyperemia captured in the eye image. The eye image may be an image preprocessed by the above-described preprocessing algorithms. For example, the eye image may be an image on which preprocessing including second cropping, first masking, and resizing is performed.

To train the first prediction model, an artificial intelligence model may be prepared.

Examples of the artificial intelligence model may be a support-vector machine (SVM), Random Forest, Gradient Boosting Algorithm, ResNet, VGG, GoogLeNet, MobileNet, and Vision Transformer.

Next, the eye images included in the prepared plurality of training data sets are input to the artificial intelligence model, and training is performed using the evaluation value corresponding to each of the input eye images and an output value output from the artificial intelligence model.

When the first prediction model includes the first left eye prediction model and the first right eye prediction model, the plurality of training data sets for training the first left eye prediction model may include left eye images and evaluation values for conjunctival hyperemia captured in the left eye images, and the plurality of training data sets for training a first right eye prediction model may include right eye images and evaluation values for conjunctival hyperemia captured in the right eye images. In the meantime, in order to increase the number of training data sets, the plurality of training data sets for training the first left eye prediction model may include right eye images on which lateral inversion is processed and evaluation values for conjunctival hyperemia captured in the right eye images, and the plurality of training data sets for training the first right eye prediction model may include left eye images on which lateral inversion is processed and evaluation values for conjunctival hyperemia captured in the left eye images.

When it is intended not to dualize the first prediction model, but to realize the first prediction model as one model, the plurality of training data sets may include right eye images and evaluation values for conjunctival hyperemia captured in the right eye images, or may include left eye images on which lateral inversion is performed and evaluation values for conjunctival hyperemia captured in the left eye images. Alternatively, the plurality of training data sets may include left eye images and evaluation values for conjunctival hyperemia captured in the left eye images, or may include right eye images on which lateral inversion is performed and evaluation values for conjunctival hyperemia captured in the right eye images.

In the meantime, in training the first prediction model, in order to predict whether there is conjunctival hyperemia without distinguishing between right eye images and left eye images, all right eye images, right eye images on which lateral inversion is performed, left eye images, and left eye images on which lateral inversion is performed are used as training data for training one model.

For example, when the first prediction model includes the first left eye prediction model and the first right eye prediction model, the plurality of training data sets for training the first left eye prediction model may include: left eye images and evaluation values for conjunctival hyperemia captured in the left eye images; and right eye images on which lateral inversion is performed and evaluation values for conjunctival hyperemia captured in the right eye images, and the plurality of training data sets for training the first right eye prediction model may include: right eye images and evaluation values for conjunctival hyperemia captured in the right eye images; and left eye images on which lateral inversion is performed and evaluation values for conjunctival hyperemia captured in the left eye images.

When it is intended not to dualize the first prediction model, but to realize the first prediction model as one model, the plurality of training data sets may include: right eye images and evaluation values for conjunctival hyperemia captured in the right eye images; right eye images on which lateral inversion is performed and evaluation values for conjunctival hyperemia captured in the right eye images; left eye images and evaluation values for conjunctival hyperemia captured in the left eye images; and left eye images on which lateral inversion is performed and evaluation values for conjunctival hyperemia captured in the left eye images.

(2) Second Prediction Model

Purpose and Operation of Second Prediction Model

The second prediction model is a model for predicting whether there is conjunctival edema.

The second prediction model may receive an eye image as input data and may output a probability value of the presence of conjunctival edema captured in the input eye image.

When the second prediction model includes a second left eye prediction model and a second right eye prediction model, the second left eye prediction model may receive a left eye image and output a probability value of the presence of conjunctival edema captured in the left eye image, and the second right eye prediction model may receive a right eye image and output a probability value of the presence of conjunctival edema captured in the right eye image.

When the second prediction model is not dualized and is realized as one model, the second prediction model may receive either a right eye image or a left eye image to output a probability value of the presence of conjunctival edema captured in the input image, and may receive the other image to output a probability value of the presence of conjunctival edema captured in the input image.

The eye image may be an image preprocessed by the above-described preprocessing algorithms.

For example, the eye image may be an image on which preprocessing according to second cropping is performed.

As another example, the eye image may be an image on which preprocessing including second cropping and resizing is performed.

As still another example, the eye image may be an image on which preprocessing including second cropping, first masking, and resizing is performed.

As yet still another example, the eye image may be an image on which preprocessing including second cropping, first masking, lateral inversion, and resizing is performed.

In the present specification, the second prediction model may be called a conjunctival edema prediction model.

Training of Second Prediction Model

To train the second prediction model, a plurality of training data sets may be prepared. A training data set may include an eye image and an evaluation value for the presence of conjunctival edema captured in the eye image. The eye image may be an image preprocessed by the above-described preprocessing algorithms. For example, the eye image may be an image on which preprocessing including second cropping, first masking, and resizing is performed.

To train the second prediction model, an artificial intelligence model may be prepared.

Examples of the artificial intelligence model may be a support-vector machine (SVM), Random Forest, Gradient Boosting Algorithm, ResNet, VGG, GoogLeNet, MobileNet, and Vision Transformer.

Next, the eye images included in the prepared plurality of training data sets are input to the artificial intelligence model, and training is performed using the evaluation value corresponding to each of the input eye images and an output value output from the artificial intelligence model.

When the second prediction model includes the second left eye prediction model and the second right eye prediction model, the plurality of training data sets for training the second left eye prediction model may include left eye images and evaluation values for the presence of conjunctival edema captured in the left eye images, and the plurality of training data sets for training the second right eye prediction model may include right eye images and evaluation values for the presence of conjunctival edema captured in the right eye images. In the meantime, in order to increase the number of training data sets, the plurality of training data sets for training the second left eye prediction model may include right eye images on which lateral inversion is processed and evaluation values for the presence of conjunctival edema captured in the right eye images, and the plurality of training data sets for training the second right eye prediction model may include left eye images on which lateral inversion is processed and evaluation values for the presence of conjunctival edema captured in the left eye images.

When it is intended not to dualize the second prediction model, but to realize the second prediction model as one model, the plurality of training data sets may include right eye images and evaluation values for the presence of conjunctival edema captured in the right eye images, or may include left eye images on which lateral inversion is performed and evaluation values for the presence of conjunctival edema captured in the left eye images. Alternatively, the plurality of training data sets may include left eye images and evaluation values for the presence of conjunctival edema captured in the left eye images, or may include right eye images on which lateral inversion is performed and evaluation values for the presence of conjunctival edema captured in the right eye images.

In the meantime, in training the second prediction model, in order to predict whether there is conjunctival edema without distinguishing between right eye images and left eye images, all right eye images, right eye images on which lateral inversion is performed, left eye images, and left eye images on which lateral inversion is performed are used as training data for training one model.

For example, when the second prediction model includes the second left eye prediction model and the second right eye prediction model, the plurality of training data sets for training the second left eye prediction model may include: left eye images and evaluation values for conjunctival edema captured in the left eye images; and right eye images on which lateral inversion is performed and evaluation values for conjunctival edema captured in the right eye images, and the plurality of training data sets for training the second right eye prediction model may include: right eye images and evaluation values for conjunctival edema captured in the right eye images; and left eye images on which lateral inversion is performed and evaluation values for conjunctival edema captured in the left eye images.

When it is intended not to dualize the second prediction model, but to realize the second prediction model as one model, the plurality of training data sets may include: right eye images and evaluation values for conjunctival edema captured in the right eye images; right eye images on which lateral inversion is performed and evaluation values for conjunctival edema captured in the right eye images; left eye images and evaluation values for conjunctival edema captured in the left eye images; and left eye images on which lateral inversion is performed and evaluation values for conjunctival edema captured in the left eye images.

(3) Third Prediction Model

Purpose and Operation of Third Prediction Model

The third prediction model is a model for predicting whether there is lacrimal edema.

The third prediction model may receive an eye image as input data and may output a probability value of the presence of lacrimal edema captured in the input eye image.

When the third prediction model includes a third left eye prediction model and a third right eye prediction model, the third left eye prediction model may receive a left eye image and output a probability value of the presence of lacrimal edema captured in the left eye image, and the third right eye prediction model may receive a right eye image and output a probability value of the presence of lacrimal edema captured in the right eye image.

When the third prediction model is not dualized and is realized as one model, the third prediction model may receive either a right eye image or a left eye image to output a probability value of the presence of lacrimal edema captured in the input image, and may receive the other image to output a probability value of the presence of lacrimal edema captured in the input image.

The eye image may be an image preprocessed by the above-described preprocessing algorithms.

For example, the eye image may be an image on which preprocessing according to second cropping is performed.

As another example, the eye image may be an image on which preprocessing including second cropping and resizing is performed.

As still another example, the eye image may be an image on which preprocessing including second cropping, first masking, and resizing is performed.

As yet still another example, the eye image may be an image on which preprocessing including second cropping, first masking, lateral inversion, and resizing is performed.

In the present specification, the third prediction model may be called a lacrimal edema prediction model.

Training of Third Prediction Model

To train the third prediction model, a plurality of training data sets may be prepared. A training data set may include an eye image and an evaluation value for the presence of lacrimal edema captured in the eye image. The eye image may be an image preprocessed by the above-described preprocessing algorithms. For example, the eye image may be an image on which preprocessing including second cropping, first masking, and resizing is performed.

To train the third prediction model, an artificial intelligence model may be prepared.

Examples of the artificial intelligence model may be a support-vector machine (SVM), Random Forest, Gradient Boosting Algorithm, ResNet, VGG, GoogLeNet, MobileNet, and Vision Transformer.

Next, the eye images included in the prepared plurality of training data sets are input to the artificial intelligence model, and training is performed using the evaluation value corresponding to each of the input eye images and an output value output from the artificial intelligence model.

When the third prediction model includes the third left eye prediction model and the third right eye prediction model, the plurality of training data sets for training the third left eye prediction model may include left eye images and evaluation values for the presence of lacrimal edema captured in the left eye images, and the plurality of training data sets for training the third right eye prediction model may include right eye images and evaluation values for the presence of lacrimal edema captured in the right eye images. In the meantime, in order to increase the number of training data sets, the plurality of training data sets for training the third left eye prediction model may include right eye images on which lateral inversion is processed and evaluation values for the presence of lacrimal edema captured in the right eye images, and the plurality of training data sets for training the third right eye prediction model may include left eye images on which lateral inversion is processed and evaluation values for the presence of lacrimal edema captured in the left eye images.

When it is intended not to dualize the third prediction model, but to realize the third prediction model as one model, the plurality of training data sets may include right eye images and evaluation values for the presence of lacrimal edema captured in the right eye images, or may include left eye images on which lateral inversion is performed and evaluation values for the presence of lacrimal edema captured in the left eye images. Alternatively, the plurality of training data sets may include left eye images and evaluation values for the presence of lacrimal edema captured in the left eye images, or may include right eye images on which lateral inversion is performed and evaluation values for the presence of lacrimal edema captured in the right eye images.

In the meantime, in training the third prediction model, in order to predict whether there is lacrimal edema without distinguishing between right eye images and left eye images, all right eye images, right eye images on which lateral inversion is performed, left eye images, and left eye images on which lateral inversion is performed are used as training data for training one model.

For example, when the third prediction model includes the third left eye prediction model and the third right eye prediction model, the plurality of training data sets for training the third left eye prediction model may include: left eye images and evaluation values for lacrimal edema captured in the left eye images; and right eye images on which lateral inversion is performed and evaluation values for lacrimal edema captured in the right eye images, and the plurality of training data sets for training the third right eye prediction model may include: right eye images and evaluation values for lacrimal edema captured in the right eye images; and left eye images on which lateral inversion is performed and evaluation values for lacrimal edema captured in the left eye images.

When it is intended not to dualize the third prediction model, but to realize the third prediction model as one model, the plurality of training data sets may include: right eye images and evaluation values for lacrimal edema captured in the right eye images; right eye images on which lateral inversion is performed and evaluation values for lacrimal edema captured in the right eye images; left eye images and evaluation values for lacrimal edema captured in the left eye images; and left eye images on which lateral inversion is performed, and evaluation values for lacrimal edema captured in the left eye images.

(4) Fourth Prediction Model

Purpose and Operation of Fourth Prediction Model

The fourth prediction model is a model for predicting whether there is eyelid redness.

The fourth prediction model may receive an eye image as input data and may output a probability value of the presence of eyelid redness captured in the input eye image.

When the fourth prediction model includes a fourth left eye prediction model and a fourth right eye prediction model, the fourth left eye prediction model may receive a left eye image and output a probability value of the presence of eyelid redness captured in the left eye image, and the fourth right eye prediction model may receive a right eye image and output a probability value of the presence of eyelid redness captured in the right eye image.

When the fourth prediction model is not dualized and is realized as one model, the fourth prediction model may receive either a right eye image or a left eye image to output a probability value of the presence of eyelid redness captured in the input image, and may receive the other image to output a probability value of the presence of eyelid redness captured in the input image.

The eye image may be an image preprocessed by the above-described preprocessing algorithms.

For example, the eye image may be an image on which preprocessing according to third cropping is performed.

As another example, the eye image may be an image on which preprocessing including third cropping and resizing is performed.

As still another example, the eye image may be an image on which preprocessing including third cropping, lateral inversion, and resizing is performed.

As still another example, the eye image may be an image on which preprocessing including third cropping, second masking, and resizing is performed.

As yet still another example, the eye image may be an image on which preprocessing including third cropping, second masking, lateral inversion, and resizing is performed.

In the present specification, the fourth prediction model may be called an eyelid redness prediction model.

Training of Fourth Prediction Model

To train the fourth prediction model, a plurality of training data sets may be prepared. A training data set may include an eye image and an evaluation value for eyelid redness captured in the eye image. The eye image may be an image preprocessed by the above-described preprocessing algorithms. For example, the eye image may be an image on which preprocessing including second cropping, first masking, and resizing is performed.

To train the fourth prediction model, an artificial intelligence model may be prepared.

Examples of the artificial intelligence model may be a support-vector machine (SVM), Random Forest, Gradient Boosting Algorithm, ResNet, VGG, GoogLeNet, MobileNet, and Vision Transformer.

Next, the eye images included in the prepared plurality of training data sets are input to the artificial intelligence model, and training is performed using the evaluation value corresponding to each of the input eye images and an output value output from the artificial intelligence model.

When the fourth prediction model include the fourth left eye prediction model and the fourth right eye prediction model, the plurality of training data sets for training the fourth left eye prediction model may include left eye images and evaluation values for eyelid redness captured in the left eye images, and the plurality of training data sets for training the fourth right eye prediction model may include right eye images and evaluation values for eyelid redness captured in the right eye images. In the meantime, in order to increase the number of training data sets, the plurality of training data sets for training the fourth left eye prediction model may include right eye images on which lateral inversion is processed and evaluation values for eyelid redness captured in the right eye images, and the plurality of training data sets for training the fourth right eye prediction model may include left eye images on which lateral inversion is processed and evaluation values for eyelid redness captured in the left eye images.

When it is intended not to dualize the fourth prediction model, but to realize the fourth prediction model as one model, the plurality of training data sets may include right eye images and evaluation values for eyelid redness captured in the right eye images, or may include left eye images on which lateral inversion is performed and evaluation values for eyelid redness captured in the left eye images. Alternatively, the plurality of training data sets may include left eye images and evaluation values for eyelid redness captured in the left eye images, or may include right eye images on which lateral inversion is performed and evaluation values for eyelid redness captured in the right eye images.

In the meantime, in training the fourth prediction model, in order to predict whether there is eyelid redness without distinguishing between right eye images and left eye images, all right eye images, right eye images on which lateral inversion is performed, left eye images, and left eye images on which lateral inversion is performed are used as training data for training one model.

For example, when the fourth prediction model includes the fourth left eye prediction model and the fourth right eye prediction model, the plurality of training data sets for training the fourth left eye prediction model may include: left eye images and evaluation values for eyelid redness captured in the left eye images; and right eye images on which lateral inversion is performed and evaluation values for eyelid redness captured in the right eye images, and the plurality of training data sets for training the fourth right eye prediction model may include: right eye images and evaluation values for eyelid redness captured in the right eye images; and left eye images on which lateral inversion is performed and evaluation values for eyelid redness captured in the left eye images.

When it is intended not to dualize the fourth prediction model, but to realize the fourth prediction model as one model, the plurality of training data sets may include: right eye images and evaluation values for eyelid redness captured in the right eye images; right eye images on which lateral inversion is performed and evaluation values for eyelid redness captured in the right eye images; left eye images and evaluation values for eyelid redness captured in the left eye images; and left eye images on which lateral inversion is performed and evaluation values for eyelid redness captured in the left eye images.

(5) Fifth Prediction Model

Purpose and Operation of Fifth Prediction Model

The fifth prediction model is a model for predicting whether there is eyelid edema.

The fifth prediction model may receive an eye image as input data and may output a probability value of the presence of eyelid edema captured in the input eye image.

When the fifth prediction model includes a fifth left eye prediction model and a fifth right eye prediction model, the fifth left eye prediction model may receive a left eye image and output a probability value of the presence of eyelid edema captured in the left eye image, and the fifth right eye prediction model may receive a right eye image and output a probability value of the presence of eyelid edema captured in the right eye image.

When the fifth prediction model is not dualized and is realized as one model, the fifth prediction model may receive either a right eye image or a left eye image to output a probability value of the presence of eyelid edema captured in the input image, and may receive the other image to output a probability value of the presence of eyelid edema captured in the input image.

The eye image may be an image preprocessed by the above-described preprocessing algorithms.

For example, the eye image may be an image on which preprocessing according to third cropping is performed.

As another example, the eye image may be an image on which preprocessing including third cropping and resizing is performed.

As still another example, the eye image may be an image on which preprocessing including third cropping, lateral inversion, and resizing is performed.

As still another example, the eye image may be an image on which preprocessing including third cropping, second masking, and resizing is performed.

As yet still another example, the eye image may be an image on which preprocessing including third cropping, second masking, lateral inversion, and resizing is performed.

In the present specification, the fifth prediction model may be called an eyelid edema prediction model.

Training of Fifth Prediction Model

To train the fifth prediction model, a plurality of training data sets may be prepared. A training data set may include an eye image and an evaluation value for the presence of eyelid edema captured in the eye image. The eye image may be an image preprocessed by the above-described preprocessing algorithms. For example, the eye image may be an image on which preprocessing including third cropping, second masking, and resizing is performed.

To train the fifth prediction model, an artificial intelligence model may be prepared.

Examples of the artificial intelligence model may be a support-vector machine (SVM), Random Forest, Gradient Boosting Algorithm, ResNet, VGG, GoogLeNet, MobileNet, and Vision Transformer.

Next, the eye images included in the prepared plurality of training data sets are input to the artificial intelligence model, and training is performed using the evaluation value corresponding to each of the input eye images and an output value output from the artificial intelligence model.

When the fifth prediction model includes the fifth left eye prediction model and the fifth right eye prediction model, the plurality of training data sets for training the fifth left eye prediction model may include left eye images and evaluation values for the presence of eyelid edema captured in the left eye images, and the plurality of training data sets for training the fifth right eye prediction model may include right eye images and evaluation values for the presence of eyelid edema captured in the right eye images. In the meantime, in order to increase the number of training data sets, the plurality of training data sets for training the fifth left eye prediction model may include right eye images on which lateral inversion is processed and evaluation values for the presence of eyelid edema captured in the right eye images, and the plurality of training data sets for training the fifth right eye prediction model may include left eye images on which lateral inversion is processed and evaluation values for the presence of eyelid edema captured in the left eye images.

When it is intended not to dualize the fifth prediction model, but to realize the fifth prediction model as one model, the plurality of training data sets may include right eye images and evaluation values for the presence of eyelid edema captured in the right eye images, or may include left eye images on which lateral inversion is performed and evaluation values for the presence of eyelid edema captured in the left eye images. Alternatively, the plurality of training data sets may include left eye images and evaluation values for the presence of eyelid edema captured in the left eye images, or may include right eye images on which lateral inversion is performed and evaluation values for the presence of eyelid edema captured in the right eye images.

In the meantime, in training the fifth prediction model, in order to predict whether there is eyelid edema without distinguishing between right eye images and left eye images, all right eye images, right eye images on which lateral inversion is performed, left eye images, and left eye images on which lateral inversion is performed are used as training data for training one model.

For example, when the fifth prediction model includes the fifth left eye prediction model and the fifth right eye prediction model, the plurality of training data sets for training the fifth left eye prediction model may include: left eye images and evaluation values for eyelid edema captured in the left eye images; and right eye images on which lateral inversion is performed and evaluation values for eyelid edema captured in the right eye images, and the plurality of training data sets for training the fifth right eye prediction model may include: right eye images and evaluation values for eyelid edema captured in the right eye images; and left eye images on which lateral inversion is performed and evaluation values for eyelid edema captured in the left eye images.

When it is intended not to dualize the fifth prediction model, but to realize the fifth prediction model as one model, the plurality of training data sets may include: right eye images and evaluation values for eyelid edema captured in the right eye images; right eye images on which lateral inversion is performed and evaluation values for eyelid edema captured in the right eye images; left eye images and evaluation values for eyelid edema captured in the left eye images; and left eye images on which lateral inversion is performed and evaluation values for eyelid edema captured in the left eye images.

The training of the prediction models may be performed by an electronic device, and in particular, may be performed by the server 20 described above. Furthermore, the training of the prediction models by the electronic device or the server 20 means a series of processes for enabling output values of the prediction models for input data to be values similar to output values labelled with the input data. To this end, the electronic device or the server 20 may use the differences between the output values of the prediction models and the labelled values to change a weight value of each of the nodes included in the prediction models. Herein, the electronic device or the server 20 may determine the amount of change in the weight value of each of the nodes by using various feedback functions.

Hereinafter, the following methods through the above-described system 1 will be described: a method of predicting each symptom related to a clinical activity score for thyroid eye disease by preprocessing an eye image and inputting the preprocessed eye image to the above-described prediction models; a method of predicting a clinical activity score on the basis of a prediction result for each symptom; and a method of monitoring a prediction result of a clinical activity score and giving guidance or recommendation according to the monitored result so that a user visits the hospital and has a medical examination.

5. Conjunctival Hyperemia Prediction Method

The conjunctival hyperemia prediction method described in the present application may be performed by the server 20.

Figure 23:
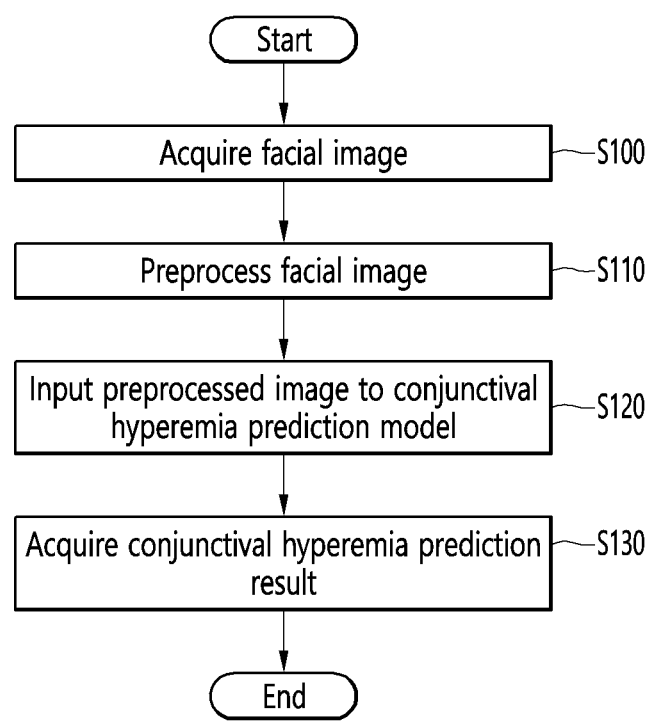
FIG. 23 is a flowchart illustrating a conjunctival hyperemia prediction method.

FIG. 23 is a flowchart illustrating a conjunctival hyperemia prediction method.

Referring to FIG. 23, the server 20 acquires a facial image in step S100, preprocesses the acquired facial image in step S110, inputs the preprocessed image to the above-described first prediction model (conjunctival hyperemia prediction model) in step S120, and acquires an output value of the first prediction model in step S130.

Acquisition of Facial Image

The server 20 acquires a facial image in step S100. The server 20 may acquire the facial image from the user terminal 10.

Preprocessing of Facial Image

The server 20 may preprocess the acquired facial image in step S110. The server 20 may perform, on the acquired facial image, iris segmentation, eye outline segmentation, masking, cropping, and resizing, which are described above.

Segmentation Processing

The server 20 may perform the iris segmentation and the eye outline segmentation, and the server 20 may thus determine the pixels corresponding to the iris and the pixels corresponding to the inside of the outline of the eye within the acquired facial image. The server 20 may determine the coordinate values of the pixels corresponding to the iris and the coordinate values of the pixels corresponding to the inside of the outline of the eye.

Masking Processing

The server 20 may perform the first masking on the facial image on the basis of information on the determined pixels. Through the first masking processing, the server 20 may remove the pixel values of the pixels excluding the pixels corresponding to the conjunctiva exposed to the outside and the lacrimal caruncle among the pixels included in the facial image. Accordingly, the pixel values of the pixels corresponding to the conjunctiva and lacrimal caruncle of the left eye and to the conjunctiva and lacrimal caruncle of the right eye may remain to be the original pixel values, but the pixel values of the pixels corresponding to the iris (or cornea) of the left eye, to the iris (or cornea) of the right eye, to the outside of the outline of the left eye, and to the outside of the outline of the right eye may be removed or changed to other values.

Cropping Processing

The server 20 may crop the masked facial image. The server 20 may crop the masked facial image to generate a left eye cropped image and a right eye cropped image. In performing the conjunctival hyperemia prediction method, the server 20 may use the second cropping (eye outline cropping) method among the cropping methods described above. Since the second cropping method has already been described in detail, a detailed description thereof will be omitted here.

Resizing Processing and Lateral Inversion Processing

The server 20 may resize the size of the left eye cropped image and the size of the right eye cropped image to a predetermined size.

In the meantime, when the first prediction model is not dualized, but realized as one model, the server 20 may laterally invert either the left eye cropped image or the right eye cropped image as described above. The server 20 does not laterally invert the other among the left eye cropped image and the right eye cropped image. Herein, it is determined that the criterion for determining which one of the left eye image and the right eye image is subjected to lateral inversion is the same as the criterion applied when the first prediction model is trained. That is, in training the first prediction model, when the left eye image is inverted and the right eye image is not inverted, the server 20 inverts the left eye image and does not invert the right eye image, similarly.

As described above, in realizing the first prediction model, when the first prediction model is dualized to the first left eye prediction model and the first right eye prediction model, the server 20 may not perform lateral inversion processing.

In the meantime, it has been described that when preprocessing is performed, segmentation, masking processing, cropping processing, resizing processing, and lateral inversion processing are performed, but the sequence of these types of preprocessing may be changed within a range capable of achieving the purpose of the conjunctival hyperemia prediction method disclosed in the present application.

Input of Preprocessed Image

The server 20 may input the preprocessed image to the first prediction model in step S120.

When the first prediction model is not dualized and is realized as one model, the server 20 inputs the right eye preprocessed image and the laterally inverted left eye preprocessed image to the first prediction model in order.

In realizing the first prediction model, when the first prediction model is dualized to the first left eye prediction model and the first right eye prediction model, the server 20 inputs the left eye preprocessed image to the first left eye prediction model and inputs the right eye preprocessed image to the first right eye prediction model. Alternatively, the server 20 may input the left eye preprocessed image to the first left eye prediction model, may input the laterally inverted left eye preprocessed image to the first right eye prediction model, may input the right eye preprocessed image to the first right eye prediction model, and may input the laterally inverted right eye preprocessed image to the first left eye prediction model.

In realizing the first prediction model, when the first prediction model is not dualized and is realized as one model and, simultaneously, is trained to be capable of determining whether there is conjunctival hyperemia without distinguishing between a left eye image and a right eye image, the server 20 may input the left eye preprocessed image and the right eye preprocessed image to the first prediction model without lateral inversion. Alternatively, the server 20 may input the left eye preprocessed image, the laterally inverted left eye preprocessed image, the right eye preprocessed image, and the laterally inverted right eye preprocessed image to the first prediction model.

Conjunctival Hyperemia Prediction Result

The server 20 may output a result value output from the first prediction model in step S130. The result value may be a probability value that is predicted with respect to conjunctival hyperemia captured in an image. On the basis of a predetermined threshold value, when the predicted probability value is equal to or greater than the threshold value, the server 20 determines that the conjunctiva is hyperemic, or when the predicted probability value is less than the threshold value, the server 20 determines that the conjunctiva is not hyperemic.

The server 20 may acquire both a prediction result for the left eye and a prediction result for the right eye.

When the server 20 inputs the left eye preprocessed image to the first left eye prediction model, inputs the laterally inverted left eye preprocessed image to the first right eye prediction model, inputs the right eye preprocessed image to the first right eye prediction model, and inputs the laterally inverted right eye preprocessed image to the first left eye prediction model, the server 20 may obtain a prediction result for the left eye considering both a result obtained by inputting the left eye preprocessed image to the first left eye prediction model and a result obtained by inputting the laterally inverted left eye preprocessed image to the first right eye prediction model. Herein, the server 20 may obtain a prediction result for the right eye considering both a result obtained by inputting the right eye preprocessed image to the first right eye prediction model and a result obtained by inputting the laterally inverted right eye preprocessed image to the first left eye prediction model.

For example, the server 20 may obtain a prediction result for the left eye on the basis of whether an average value of the result obtained by inputting the left eye preprocessed image to the first left eye prediction model and the result obtained by inputting the laterally inverted left eye preprocessed image to the first right eye prediction model is equal to or greater than the threshold value.

As another example, when a value of either the result obtained by inputting the left eye preprocessed image to the first left eye prediction model or the result obtained by inputting the laterally inverted left eye preprocessed image to the first right eye prediction model is equal to or greater than the above-described threshold value, the server 20 may predict that the conjunctiva of the left eye is hyperemic.

As still another example, when both the result obtained by inputting the left eye preprocessed image to the first left eye prediction model and the result obtained by inputting the laterally inverted left eye preprocessed image to the first right eye prediction model are equal to or greater than the above-described threshold value, the server 20 may predict that the conjunctiva of the left eye is hyperemic.

When the server 20 inputs the left eye preprocessed image, the laterally inverted left eye preprocessed image, the right eye preprocessed image, and the laterally inverted right eye preprocessed image to the first prediction model that is not dualized, the server 20 may obtain a prediction result for the left eye considering both a result obtained by inputting the left eye preprocessed image to the first prediction model and a result obtained by inputting the laterally inverted left eye preprocessed image to the first prediction model. Herein, the server 20 may obtain a prediction result for the right eye considering both a result obtained by inputting the right eye preprocessed image to the first prediction model and a result obtained by inputting the laterally inverted right eye preprocessed image to the first prediction model.

For example, the server 20 may obtain a prediction result for the left eye on the basis of whether an average value of the result obtained by inputting the left eye preprocessed image to the first prediction model and the result obtained by inputting the laterally inverted left eye preprocessed image to the first prediction model is equal to or greater than the threshold value.

As another example, when a value of either the result obtained by inputting the left eye preprocessed image to the first prediction model or the result obtained by inputting the laterally inverted left eye preprocessed image to the first prediction model is equal to or greater than the above-described threshold value, the server 20 may predict that the conjunctiva of the left eye is hyperemic.

As still another example, when both the result obtained by inputting the left eye preprocessed image to the first prediction model and the result obtained by inputting the laterally inverted left eye preprocessed image to the first prediction model are equal to or greater than the above-described threshold value, the server 20 may predict that the conjunctiva of the left eye is hyperemic.

The above-described method may be similarly applied in determining whether there is conjunctival hyperemia of the right eye.

6. Conjunctival Edema Prediction Method

The conjunctival edema prediction method described in the present application may be performed by the server 20.

Figure 24:
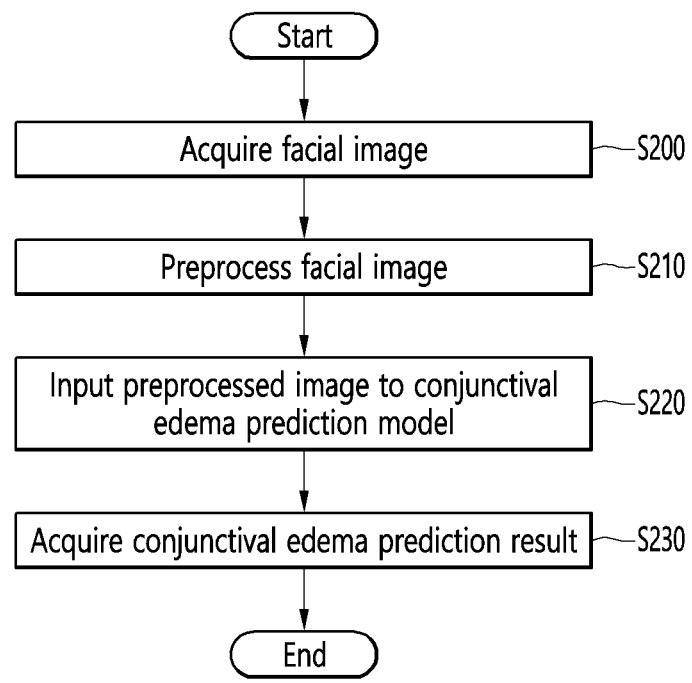
FIG. 24 is a flowchart illustrating a conjunctival edema prediction method.

FIG. 24 is a flowchart illustrating a conjunctival edema prediction method.

Referring to FIG. 24, the server 20 acquires a facial image in step S200, preprocesses the acquired facial image in step S210, inputs the preprocessed image to the above-describe second prediction model (conjunctival edema prediction model) in step S220, and acquires an output value of the second prediction model in step S230.

The conjunctival edema prediction method is the same as or very similar to the conjunctival hyperemia prediction method except that the second prediction model is used instead of the first prediction model and a finally acquired result value is a predicted value for whether there is conjunctival edema, so a detailed description of the conjunctival edema prediction method will be omitted.

7. Lacrimal Edema Prediction Method

The lacrimal edema prediction method described in the present application may be performed by the server 20.

Figure 25:
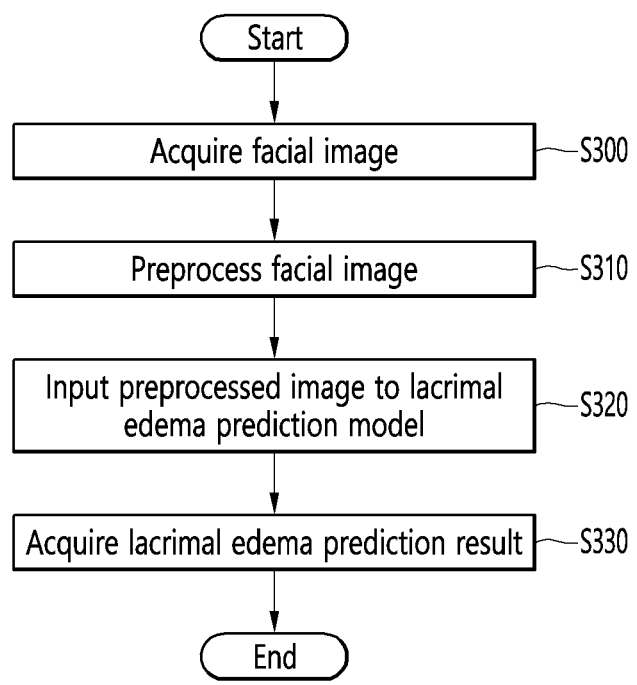
FIG. 25 is a flowchart illustrating a lacrimal edema prediction method.

FIG. 25 is a flowchart illustrating a lacrimal edema prediction method.

Referring to FIG. 25, the server 20 acquires a facial image in step S300, preprocesses the acquired facial image in step S310, inputs the preprocessed image to the above-described third prediction model (lacrimal edema prediction model) in step S320, and acquires an output value of the third prediction model in step S330.

The lacrimal edema prediction method is the same as or very similar to the conjunctival hyperemia prediction method except that the third prediction model is used instead of the first prediction model, so a detailed description of the conjunctival edema prediction method will be omitted.

As described above, the conjunctival hyperemia prediction method, the conjunctival edema prediction method, and the lacrimal edema prediction method use the same image preprocessing methods, but only the prediction models to which the preprocessed images are input are different from each other. Therefore, after image preprocessing as described above, the images may be input to different prediction models.

However, it has been described that the lacrimal edema prediction method uses the same image preprocessing methods as the conjunctival hyperemia and conjunctival edema prediction methods, but in some cases, the lacrimal edema prediction method may use the images preprocessed in a different way. For example, a preprocessed image may be used that is cropped such that the image includes a lacrimal caruncle and part of an iris. Alternatively, a preprocessed image may be used that is cropped such that the image does not include an iris, but includes a lacrimal caruncle.

8. Eyelid Redness Prediction Method

The eyelid redness prediction method described in the present application may be performed by the server 20.

Figure 26:
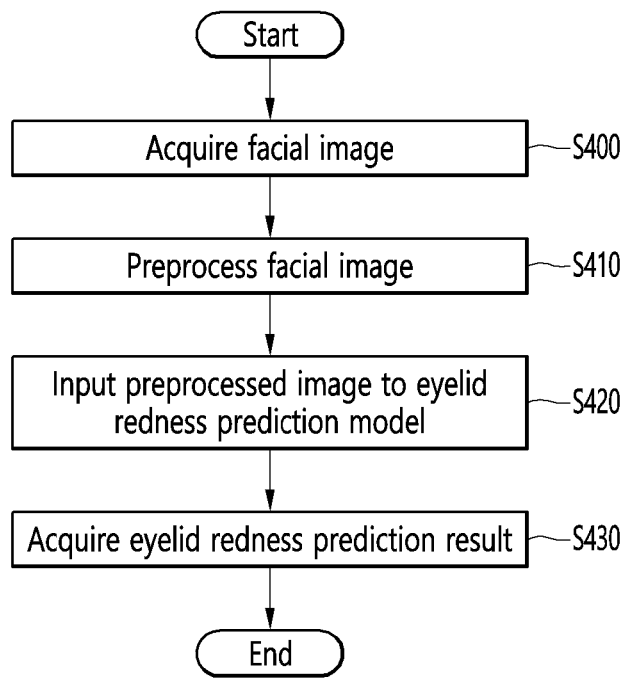
FIG. 26 is a flowchart illustrating an eyelid redness prediction method.

FIG. 26 is a flowchart illustrating an eyelid redness prediction method.

Referring to FIG. 26, the server 20 acquires a facial image in step S400, preprocesses the acquired facial image in step S410, inputs the preprocessed image to the above-described fourth prediction model (eyelid redness prediction model) in step S420, and acquires an output value of the fourth prediction model in step S430.

Acquisition of Facial Image

The server 20 acquires a facial image in step S400. The server 20 may acquire the facial image from the user terminal 10.

Preprocessing of Facial Image

The server 20 may preprocess the acquired facial image in step S410. The server 20 may perform, on the acquired facial image, iris segmentation, eye outline segmentation, masking, cropping, and resizing, which are described above.

Segmentation Processing

The server 20 may perform the iris segmentation and the eye outline segmentation, and the server 20 may thus determine the pixels corresponding to the iris and the pixels corresponding to the inside of the outline of the eye within the acquired facial image. The server 20 may determine the coordinate values of the pixels corresponding to the iris and the coordinate values of the pixels corresponding to the inside of the outline of the eye.

However, in performing the eyelid redness prediction method, as described later, iris segmentation needs to be performed when masking processing is performed, but it is allowed not to perform iris segmentation when masking processing is not performed.

Masking Processing

The server 20 may perform the second masking on the facial image on the basis of information on the determined pixels. Through the second masking processing, the server 20 may remove the pixel values of the pixels corresponding to the iris (cornea) exposed to the outside among the pixels included in the facial image. Accordingly, the pixel values of the pixels corresponding to the region excluding the iris (cornea) of the left eye and the iris (cornea) of the right eye may remain to be the original pixel values, but the pixel values of the pixels corresponding to the iris (or cornea) of the left eye and the iris (or cornea) of the right eye may be removed or changed to other values.

However, in performing the eyelid redness prediction method, performing preprocessing of masking an iris (cornea) is advantageous in several aspects, but it is allowed not to perform masking on an iris.

Cropping Processing

The server 20 may crop the masked facial image. The server 20 may crop the masked facial image to generate a left eye cropped image and a right eye cropped image. In performing the eyelid redness prediction method, the server 20 may use the third cropping (eyelid-included cropping) method among the cropping methods described above. Since the third cropping method has already been described in detail, a detailed description thereof will be omitted here.

Resizing Processing and Lateral Inversion Processing

The server 20 may resize the size of the left eye cropped image and size of the right eye cropped image to a predetermined size.

In the meantime, when the fourth prediction model is not dualized, but realized as one model, the server 20 may laterally invert either the left eye cropped image or the right eye cropped image as described above. The server 20 does not laterally invert the other among the left eye cropped image and the right eye cropped image. Herein, it is determined that the criterion for determining which one of the left eye image and the right eye image is subjected to lateral inversion is the same as the criterion applied when the fourth prediction model is trained. That is, in training the fourth prediction model, when the left eye image is inverted and the right eye image is not inverted, the server 20 inverts the left eye image and does not invert the right eye image, similarly.

As described above, in realizing the fourth prediction model, when the fourth prediction model is dualized to the fourth left eye prediction model and the fourth right eye prediction model, the server 20 may not perform lateral inversion processing.

In the meantime, it has been described that when preprocessing is performed, segmentation, masking processing, cropping processing, resizing processing, and lateral inversion processing are performed, but the sequence of these types of preprocessing may be changed within a range capable of achieving the purpose of the eyelid redness prediction method disclosed in the present application.

Input of Preprocessed Image

The server 20 may input the preprocessed image to the fourth prediction model in step S420.

When the fourth prediction model is not dualized and is realized as one model, the server 20 inputs the right eye preprocessed image and the laterally inverted left eye preprocessed image to the fourth prediction model in order.

In realizing the fourth prediction model, when the fourth prediction model is dualized to the fourth left eye prediction model and the fourth right eye prediction model, the server 20 inputs the left eye preprocessed image to the fourth left eye prediction model and inputs the right eye preprocessed image to the fourth right eye prediction model. Alternatively, the server 20 may input the left eye preprocessed image to the fourth left eye prediction model, may input the laterally inverted left eye preprocessed image to the fourth right eye prediction model, may input the right eye preprocessed image to the fourth right eye prediction model, and may input the laterally inverted right eye preprocessed image to the fourth left eye prediction model.

In realizing the fourth prediction model, when the fourth prediction model is not dualized and is realized as one model and, simultaneously, is trained to be capable of determining whether there is redness of eyelid without distinguishing between a left eye image and a right eye image, the server 20 may input the left eye preprocessed image and the right eye preprocessed image to the fourth prediction model without lateral inversion. Alternatively, the server 20 may input the left eye preprocessed image, the laterally inverted left eye preprocessed image, the right eye preprocessed image, and the laterally inverted right eye preprocessed image to the fourth prediction model.

Eyelid Redness Prediction Result

The server 20 may output a result value output from the fourth prediction model in step S430. The result value may be a probability value that is predicted with respect to eyelid redness captured in an image. On the basis of a predetermined threshold value, when the predicted probability value is equal to or greater than the threshold value, the server 20 determines that there is eyelid redness, or when the predicted probability value is less than the threshold value, the server 20 determines that there is no eyelid redness.

The server 20 may acquire both a prediction result for the left eye and a prediction result for the right eye.

When the server 20 inputs the left eye preprocessed image to the fourth left eye prediction model, inputs the laterally inverted left eye preprocessed image to the fourth right eye prediction model, inputs the right eye preprocessed image to the fourth right eye prediction model, and inputs the laterally inverted right eye preprocessed image to the fourth left eye prediction model, the server 20 may obtain a prediction result for the left eye considering both a result obtained by inputting the left eye preprocessed image to the fourth left eye prediction model and a result obtained by inputting the laterally inverted left eye preprocessed image to the fourth right eye prediction model. Herein, the server 20 may obtain a prediction result for the right eye considering both a result obtained by inputting the right eye preprocessed image to the fourth right eye prediction model and a result obtained by inputting the laterally inverted right eye preprocessed image to the fourth left eye prediction model.

For example, the server 20 may obtain a prediction result for the left eye on the basis of whether an average value of the result obtained by inputting the left eye preprocessed image to the fourth left eye prediction model and the result obtained by inputting the laterally inverted left eye preprocessed image to the fourth right eye prediction model is equal to or greater than the threshold value.

As another example, when a value of either the result obtained by inputting the left eye preprocessed image to the fourth left eye prediction model or the result obtained by inputting the laterally inverted left eye preprocessed image to the fourth right eye prediction model is equal to or greater than the above-described threshold value, the server 20 may predict that the eyelid redness is present in the left eye.

As still another example, when both the result obtained by inputting the left eye preprocessed image to the fourth left eye prediction model and the result obtained by inputting the laterally inverted left eye preprocessed image to the fourth right eye prediction model are equal to or greater than the above-described threshold value, the server 20 may predict that the conjunctiva of the left eye is hyperemic.

When the server 20 inputs the left eye preprocessed image, the laterally inverted left eye preprocessed image, the right eye preprocessed image, and the laterally inverted right eye preprocessed image to the fourth prediction model that is not dualized, the server 20 may obtain a prediction result for the left eye considering both a result obtained by inputting the left eye preprocessed image to the fourth prediction model and a result obtained by inputting the laterally inverted left eye preprocessed image to the fourth prediction model. Herein, the server 20 may obtain a prediction result for the right eye considering both a result obtained by inputting the right eye preprocessed image to the fourth prediction model and a result obtained by inputting the laterally inverted right eye preprocessed image to the fourth prediction model.

For example, the server 20 may obtain a prediction result for the left eye on the basis of whether an average value of the result obtained by inputting the left eye preprocessed image to the fourth prediction model and the result obtained by inputting the laterally inverted left eye preprocessed image to the fourth prediction model is equal to or greater than the threshold value.

As another example, when a value of either the result obtained by inputting the left eye preprocessed image to the fourth prediction model or the result obtained by inputting the laterally inverted left eye preprocessed image to the fourth prediction model is equal to or greater than the above-described threshold value, the server 20 may predict that there is eyelid redness of the left eye.

As still another example, when both the result obtained by inputting the left eye preprocessed image to the fourth prediction model and the result obtained by inputting the laterally inverted left eye preprocessed image to the fourth prediction model are equal to or greater than the above-described threshold value, the server 20 may predict that there is eyelid redness of the left eye.

The above-described method may be similarly applied in determining whether there is eyelid redness of the right eye.

9. Eyelid Edema Prediction Method

The eyelid edema prediction method described in the present application may be performed by the server 20.

Figure 27:
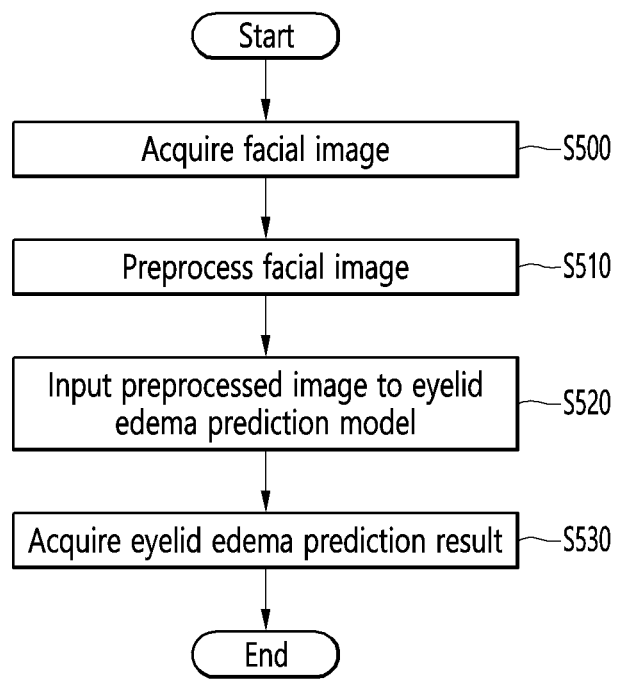
FIG. 27 is a flowchart illustrating an eyelid edema prediction method.

FIG. 27 is a flowchart illustrating an eyelid edema prediction method.

Referring to FIG. 27, the server 20 acquires a facial image in step S500, preprocesses the acquired facial image in step S510, inputs the preprocessed image to the above-described fifth prediction model (eyelid edema prediction model) in step S520, and acquires an output value of the fifth prediction model in step S530.

The eyelid edema prediction method is the same as or very similar to the eyelid redness prediction method except that the fifth prediction model is used instead of the fourth prediction model and a finally acquired result value is a predicted value for whether there is eyelid edema, so a detailed description of the eyelid edema prediction method will be omitted.

As described above, the eyelid redness prediction method and the eyelid edema prediction method use the same image preprocessing methods, but only the prediction models to which the preprocessed images are input are different from each other. Therefore, after image preprocessing as described above, the images may be input to different prediction models.

10. Method of Predicting Clinical Activity Score for Thyroid Eye Disease

Hereinafter, described will be a method, which is described in the present application, of predicting a clinical activity score for thyroid eye disease.

Figure 28:
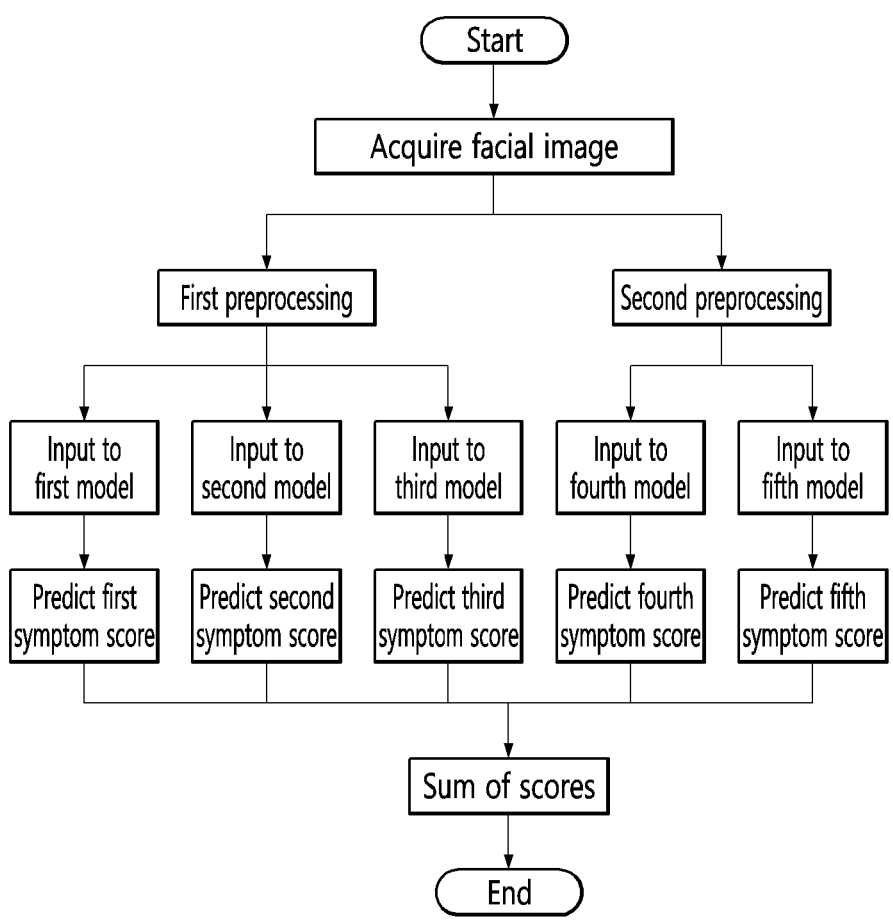
FIG. 28 is a diagram illustrating a method of predicting a clinical activity score for thyroid eye disease.

FIG. 28 is a diagram illustrating a method of predicting a clinical activity score for thyroid eye disease.

The server 20 may acquire a facial image.

The server 20 performs two different types of preprocessing on one facial image. First preprocessing (hereinafter, first preprocessing) includes iris segmentation, eye outline segmentation, first masking, second cropping (eye outline cropping), resizing, and lateral inversion, and second preprocessing (hereinafter, second preprocessing) includes iris segmentation, eye outline segmentation, second masking, third cropping (eyelid-included cropping), resizing, and lateral inversion. However, as described in the eyelid redness prediction method, iris segmentation and second masking may be omitted.

The server 20 acquires a first preprocessed image by performing first preprocessing on the acquired facial image, and the first preprocessed image includes a first left eye preprocessed image and a first right eye preprocessed image. Herein, either the first left eye preprocessed image or the first right eye preprocessed image is an image on which lateral inversion is processed. Furthermore, as already described in detail, since the first preprocessed image is an image obtained using second cropping, the number of pixels corresponding to the eyelids within the first preprocessed image is minimized and the pixels corresponding to the conjunctivas exposed to the outside and the lacrimal caruncles are included. Furthermore, the first preprocessed image is an image obtained using first masking, the pixel values of pixels corresponding to irises (or corneas) and eyelids (upper eyelid and lower eyelid) are removed, but the pixel values of pixels corresponding to the conjunctivas exposed to the outside and the lacrimal caruncles remain.

In addition, the server 20 acquires a second preprocessed image by performing second preprocessing on the acquired facial image, and the second preprocessed image includes a second left eye preprocessed image and a second right eye preprocessed image. Herein, either the second left eye preprocessed image or the second right eye preprocessed image is an image on which lateral inversion is performed. Furthermore, as already described in detail, since the second preprocessed image is an image obtained by using third cropping, the second preprocessed image includes sufficient pixels corresponding to eyelids. Furthermore, when the second masking method is used to obtain the second preprocessed image, the pixel values of the pixels corresponding to the irises (or corneas) and eyelids (upper eyelid and lower eyelid) may be removed.

The server 20 inputs the first preprocessed image (the first left eye preprocessed image and the first right eye preprocessed image) to the first prediction model in order. The server 20 obtains a result value (probability value) of the first prediction model for the first left eye preprocessed image, and determines, on the basis of the result value, whether there is conjunctival hyperemia of the left eye. In addition, the server 20 obtains a result value (probability value) of the first prediction model for the first right eye preprocessed image, and determines, on the basis of the result value, whether there is conjunctival hyperemia of the right eye.

The server 20 synthesizes a determination result for the left eye and a determination result for the right eye, and finally determines whether there is conjunctival hyperemia of both eyes. For example, when determining that there is conjunctival hyperemia of either the left eye or the right eye or both, the server 20 finally determines that there is conjunctival hyperemia.

Next, the server 20 inputs the first preprocessed image (the first left eye preprocessed image and the first right eye preprocessed image) to the second prediction model in order. The server 20 obtains a result value (probability value) of the second prediction model for the first left eye preprocessed image, and determines, on the basis of the result value, whether there is conjunctival edema of the left eye. In addition, the server 20 obtains a result value (probability value) of the second prediction model for the first right eye preprocessed image, and determines, on the basis of the result value, whether there is conjunctival edema of the right eye.

The server 20 synthesizes a determination result for the left eye and a determination result for the right eye, and finally determines whether there is conjunctival edema of both eyes. For example, when determining that there is conjunctival edema of either the left eye or the right eye or both, the server 20 finally determines that there is conjunctival edema.

Next, the server 20 inputs the first preprocessed image (the first left eye preprocessed image and the first right eye preprocessed image) to the third prediction model in order. The server 20 obtains a result value (probability value) of the third prediction model for the first left eye preprocessed image, and determines, on the basis of the result value, whether there is lacrimal edema of the left eye. In addition, the server 20 obtains a result value (probability value) of the third prediction model for the first right eye preprocessed image, and determines, on the basis of the result value, whether there is lacrimal edema of the right eye.

The server 20 synthesizes a determination result for the left eye and a determination result for the right eye, and finally determines whether there is lacrimal edema of both eyes. For example, when determining that there is lacrimal edema of either the left eye or the right eye or both, the server 20 finally determines that there is lacrimal edema.

The server 20 inputs the second preprocessed image (the second left eye preprocessed image and the second right eye preprocessed image) to the fourth prediction model in order.

The server 20 obtains a result value (probability value) of the fourth prediction model for the second left eye preprocessed image, and determines, on the basis of the result value, whether there is eyelid redness of the left eye. In addition, the server 20 obtains a result value (probability value) of the fourth prediction model for the second right eye preprocessed image, and determines, on the basis of the result value, whether there is eyelid redness of the right eye.

The server 20 synthesizes a determination result for the left eye and a determination result for the right eye, and finally determines whether there is eyelid redness of both eyes. For example, when determining that there is eyelid redness of either the left eye or the right eye or both, the server 20 finally determines that there is eyelid redness.

The server 20 inputs the second preprocessed image (the second left eye preprocessed image and the second right eye preprocessed image) to the fifth prediction model in order. The server 20 obtains a result value (probability value) of the fifth prediction model for the second left eye preprocessed image, and determines, on the basis of the result value, whether there is eyelid edema of the left eye. In addition, the server 20 obtains a result value (probability value) of the fifth prediction model for the second right eye preprocessed image, and determines, on the basis of the result value, whether there is eyelid edema of the right eye.

The server 20 synthesizes a determination result for the left eye and a determination result for the right eye, and finally determines whether there is eyelid edema of both eyes. For example, when determining that there is eyelid edema of either the left eye or the right eye or both, the server 20 finally determines that there is eyelid edema.

When it is determined that there is a symptom through a prediction model, the server 20 may give a predetermined score (for example, a score of 1) for the symptom. The server may give scores for five respective symptoms according to determination results for the five prediction models, and may also obtain a value obtained by adding all the scores.

It has been described that the above-described method, which is described in the present application, of predicting a clinical activity score for thyroid eye disease is performed by the server 20. However, the above-described method may be performed by a user terminal 10. Alternatively, preprocessing of the above-described methods may be performed by the user terminal 10, and determination for each of the symptoms may be performed by the server. That is, the above-described steps may be appropriately distributed to the user terminal 10 and the server 20 and performed.

11. Hospital Visit Recommendation Method Based on Continuous Monitoring of Clinical Activity Score for Thyroid Eye Disease Hereinafter, described will be a method of continuously monitoring a clinical activity score for thyroid eye disease, and a method of recommending a hospital visit on the basis of the monitoring method described in the present application.

FIG. 29 is a diagram illustrating a method of continuously monitoring a clinical activity score for thyroid eye disease, and a method of recommending a hospital visit on the basis of the monitoring method described in the present application.

A user terminal 10 may output a guide for acquiring a facial image, through a display 112 in step S600.

The user terminal 10 may output, through the display 112, an image (for example, an image of a user's face) captured in real time through a camera 140. Herein, the guide may be output together.

The user terminal 10 may acquire a facial image of the user's face through the camera 140 in step S610.

The user terminal 10 may transmit the acquired facial image to the server 20 in step S620.

The user terminal 10 may output, through the display, a graphical user interface (GUI) for receiving a user input with respect to spontaneous retrobulbar pain and pain on an attempted upward or downward gaze among a total of seven items considered in determining a clinical activity score for thyroid eye disease. Next, the user terminal 10 may receive the user's response to the two items in step S630. The user terminal 10 may give, on the basis of the input response of the user, a predetermined score (for example, a score of 1) for each of the items. For example, when the user provides an input that the user has spontaneous retrobulbar pain, the user terminal 10 may give a score of 1 for the item. In addition, when the user provides an input that the user has pain on an attempted upward or downward gaze, the user terminal 10 may give a score of 1 for the item.

The user terminal 10 may receive, from the server 20 in step S640, determination results or a total score thereof for redness of a conjunctiva, swelling of a conjunctiva, swelling of a lacrimal caruncle, redness of an eyelid, and swelling of an eyelid among the total of seven items considered in determining a clinical activity score for thyroid eye disease on the basis of the acquired facial image.

The user terminal 10 may calculate a final clinical activity score for thyroid eye disease in step S650 on the basis of the scores determined by the user input and the scores received from the server 20 or the scores determined on the basis of the determination results received from the server.

The user terminal 10 may store the time at which the facial image of the user is acquired, or the time at which a calculation value of the final clinical activity score for thyroid eye disease is acquired, or the corresponding time (hereinafter, referred to as measurement time, yy/mm/dd, hh:mm) in a memory 130 together with the calculated clinical activity score. Alternatively, the user terminal 10 may transmit the above-described measurement time and a clinical activity score corresponding thereto to the server 20. Herein, the server 20 may store the measurement time and the clinical activity score in association with the user terminal 10 or the user in step S660.

In the meantime, the measurement time includes information on the date. The measurement time may include both information on the date and information on the hour and/or minute. Alternatively, the measurement time may include only the information on the date, and may not include the information on the hour or minute.

The user terminal 10 may output, on the basis of the calculated clinical activity score, information for recommending that the user visit the hospital and have a detailed medical examination, through the display 112 in step S670.

When the calculated clinical activity score is less than a score of 3, the user terminal 10 may output information indicating that there is no risk of thyroid eye disease, through the display 112.

When the calculated clinical activity score is a score of 3 or 4, the user terminal 10 may output information indicating that there is no risk of thyroid eye disease, through the display 112, or may output information for recommending that the user visit the hospital and have a detailed medical examination, through the display 112, by choice.

When the calculated clinical activity score is equal to or greater than a score of 5, the user terminal 10 may output information for recommending that the user visit the hospital and have a detailed medical examination, through the display 112.

When the calculated clinical activity score is a score of 3 or 4, the clinical activity score that was measured a predetermined period of time (for example, one week) before the corresponding time point is determined, and it may be determined whether the clinical activity score was a score of 3 or 4 during the corresponding time interval (hereinafter, the monitoring time interval). Herein, when a score of 3 or 4 occurred one or more times during the monitoring time interval, the user terminal 10 outputs information for recommending that the user visit the hospital and have a detailed medical examination, through the display 112. When a score of 3 or 4 never occurred during the monitoring time interval, the user terminal 10 outputs information indicating that there is no risk of thyroid eye disease, through the display 112.

When the calculated clinical activity score is equal to or greater than a score of 3, the user terminal 10 may output information for recommending that the user visit the hospital and have a detailed medical examination, through the display 112 without additional determination for past records.

According to the above description, in outputting information to the user through the user terminal 10, outputting the information visually through the display 112 has been described as an example, but in some cases, the information may be audibly output through a speaker.

In addition, it has been described that the method of continuously monitoring a clinical activity score for thyroid eye disease, and the method of recommending a hospital visit on the basis of the monitoring method described in the present application are performed by the user terminal 10. However, the steps of the above-described methods may be appropriately distributed to the user terminal 10 and the server 20 and performed. For example, when the measurement time and the clinical activity score are transmitted to the server 20 and stored, whether a score of 3 or 4 occurred during the monitoring time interval may be determined by the server 20.

12. Experimental Example #1

(1) Preparation of Facial Images 1,020 facial images were prepared. Each of the facial images was an image including both a left eye and a right eye, and was an image obtained according to a predetermined photographing structure.

(2) Securing Labeling Information of Facial Images

For each of the 1,020 facial images, information on conjunctival hyperemia, conjunctival edema, lacrimal edema, eyelid redness, and eyelid edema for the left eye, and information on conjunctival hyperemia, conjunctival edema, lacrimal edema, eyelid redness, and eyelid edema for the right eye were secured, and the data were used as labeling data.

Among 1,020 data sets, 714 data sets were used as a training data set (training set), 102 data sets were used as a validation sets, and 204 data sets were used as a test set.

Furthermore, dividing the 1,020 data sets into a training data set, a validation set, and a test set was randomly performed 30 times, and a first training data set group to a 30th training data set group were created accordingly.

(3) Securing First Preprocessed Images and Second Preprocessed Images of Facial Images For each of the 1,020 facial images, second cropping processing (eye outline cropping) was performed on each of the left eye and the right eye in the above-described manner to secure a first left eye preprocessed image and a first right eye preprocessed image. Herein, a laterally inverted image was used as the first right eye preprocessed image, and a non-laterally inverted image was used as the first left eye preprocessed image. In the meantime, both the first left eye preprocessed image and the first right eye preprocessed image were images on which the above-described first masking processing was performed.

For each of the 1,020 facial images, third cropping processing (eyelid-included cropping) was performed on each of the left eye and the right eye in the above-described manner to secure a second left eye preprocessed image and a second right eye preprocessed image. Herein, a laterally inverted image was used as the second right eye preprocessed image, and a non-laterally inverted image was used as the second left eye preprocessed image. In the meantime, both the second left eye preprocessed image and the second right eye preprocessed image were images on which masking processing was not performed.

(4) Training of First to Fifth Prediction Models according to Experimental Example #1

The secured first preprocessed images and the secured pieces of labeling information thereof, and the secured second preprocessed images and the secured pieces of labeling information thereof were used in training the first to fifth prediction models.

As the prediction models, the models using the above-described ViT as the backbone architecture were used, and each of the prediction models was trained with unification as one model without dividing into a left eye prediction model and a right eye prediction model.

(5) Acquisition of Prediction result for each Symptom by using Prediction Models Prediction results were acquired using the test data sets for the trained first to fifth prediction models. Herein, a laterally inverted preprocessed image was used as a right eye image, and a non-laterally inverted preprocessed image was used as a left eye image.

(6) Accuracy, Sensitivity, Specificity, Positive Predictive Value (PPV), and Negative Predictive Value (NPV) of Eyelid Redness Prediction Model according to Experimental Example #1

The values shown in [Table 1] are average values of accuracy, sensitivity, specificity, PPV, and NPV measured for the first to fifth prediction models that were trained for each of the 30 data set groups according to the above-described experimental example #1.

TABLE 1

| | Accuracy (%) | Sensitivity (%) | Specificity (%) | PPV (%) | NPV (%) |
|---|---|---|---|---|---|
| Conjunctival hyperemia (first prediction model) | 80.80 | 86.84 | 76.40 | 73.58 | 89.10 |
| Conjunctival edema (second prediction model) | 89.12 | 42.18 | 94.82 | 50.39 | 93.15 |
| Lacrimal edema (third prediction model) | 88.14 | 55.54 | 92.52 | 53.14 | 93.96 |

TABLE 1-continued

|  | Accuracy (%) | Sensitivity (%) | Specificity (%) | PPV (%) | NPV (%) |
| --- | --- | --- | --- | --- | --- |
| Eyelid redness (fourth prediction model) | 72.42 | 73.94 | 71.55 | 59.10 | 84.17 |
| Eyelid edema (fifth prediction model) | 81.29 | 86.38 | 53.52 | 91.16 | 43.59 |

13. Experimental Example #2

(1) Preparation of Facial Images

The facial images used in experimental example #1 were used as they were.

(2) Securing Labeling Information of Facial Images

The pieces of labeling information of the facial images used in experimental example #1 were used as they were.

(3) Securing First Preprocessed Images and Second Preprocessed Images of Facial Images For each of the 1,020 facial images, second cropping processing (eye outline cropping) is performed on each of the left eye and the right eye in the above-described manner to secure first preprocessed images. Unlike experimental example #1, a first left eye preprocessed image not subjected to lateral inversion, a first left eye preprocessed image subjected to lateral inversion, a first right eye preprocessed image not subjected to lateral inversion, and a first right eye preprocessed image subjected to lateral inversion were secured, and were used in training. Herein, both the first left eye preprocessed image and the first right eye preprocessed image were images on which the above-described first masking processing was performed.

For each of the 1,020 facial images, third cropping processing (eyelid-included cropping) was performed on each of the left eye and the right eye in the above-described manner to secure second preprocessed images. Unlike experimental example #1, a second left eye preprocessed image not subjected to lateral inversion, a second left eye preprocessed image subjected to lateral inversion, a second right eye preprocessed image not subjected to lateral inversion, and a second right eye preprocessed image subjected to lateral inversion were secured, and were used in training. Herein, both the second left eye preprocessed image and the second right eye preprocessed image were images on which masking processing was not performed.

(4) Training of First to Fifth Prediction Models according to Experimental Example #2

The secured first preprocessed images and the secured pieces of labeling information thereof, and the secured second preprocessed images and the secured pieces of labeling information thereof were used in training the first to fifth prediction models.

As the prediction models, the models using the above-described ViT as the backbone architecture were used, and each of the prediction models was trained being dualized into a left eye prediction model and a right eye prediction model. In particular, when the left eye prediction models were trained, left eye preprocessed images not subjected to lateral inversion and right eye preprocessed images subjected to lateral inversion were used, and when the right eye prediction models were trained, right eye preprocessed images not subjected to lateral inversion and left eye preprocessed images subjected to lateral inversion were used.

(5) Acquisition of Prediction result for each Symptom by using Prediction Models Prediction results were acquired using the test data sets for the trained first to fifth prediction models. Herein, the prediction results for the right eye were acquired by inputting a right eye preprocessed image not subjected to lateral inversion to each of the right eye prediction models, and the prediction results for the left eye were acquired by inputting a left eye preprocessed image not subjected to lateral inversion to each of the left eye prediction models.

(6) Accuracy, Sensitivity, Specificity, Positive Predictive Value (PPV), and Negative Predictive Value (NPV) of Eyelid Redness Prediction Model according to Experimental Example #2

The values shown in [Table 2] are average values of accuracy, sensitivity, specificity, PPV, and NPV measured for the first to fifth prediction models that were trained for each of the 30 data set groups according to the above-described experimental example #2.

TABLE 2

|  | Accuracy (%) | Sensitivity (%) | Specificity (%) | PPV (%) | NPV (%) |
| --- | --- | --- | --- | --- | --- |
| Conjunctival hyperemia (first prediction model) | 79.54 | 87.26 | 73.99 | 71.84 | 89.19 |
| Conjunctival edema (second prediction model) | 89.22 | 45.04 | 94.61 | 52.53 | 93.48 |
| Lacrimal edema (third prediction model) | 88.35 | 49.51 | 93.70 | 55.48 | 93.20 |
| Eyelid redness (fourth prediction model) | 76.13 | 70.65 | 79.08 | 64.63 | 83.86 |
| Eyelid edema (fifth prediction model) | 81.47 | 86.51 | 54.44 | 91.22 | 44.62 |

1: System
10: User terminal
20: Server

The invention claimed is:

1. A computer-implemented method of predicting thyroid eye disease, comprising:
preparing a conjunctival hyperemia prediction model, a conjunctival edema prediction model, a lacrimal edema prediction model, an eyelid redness prediction model, and an eyelid edema prediction model,
obtaining a facial image of an object,
obtaining a first processed image and a second processed image from the facial image, wherein the first processed image is different from the second processed image,
obtaining predicted values for each of a conjunctival hyperemia, a conjunctival edema and a lacrimal edema by applying the first processed image to the conjunctival hyperemia prediction model, the conjunctival edema prediction model, and the lacrimal edema prediction model, obtaining predicted values for each of an eyelid redness and an eyelid edema by applying the second processed image to the eyelid redness prediction model and the eyelid edema prediction model, and determining a possibility of the object having thyroid eye disease based on the predicted values for the conjunctival hyperemia, the conjunctival edema, the lacrimal edema, the eyelid redness, and the eyelid edema, wherein the first processed image is an image masked a region corresponding an inner of an outline of an iris and a region corresponding an outer of an outline of an eye and cropped along a first region comprising the outline of the eye based on position information of pixels corresponding the outline of the iris comprised in the eye and position information of pixels corresponding the outline of the eye, and wherein the second processed image is an image cropped along a second region that is wider than the first region based on position information of pixels corresponding the outline of the iris comprised in the eye and position information of pixels corresponding the outline of the eye.

2. The computer-implemented method of predicting thyroid eye disease of claim 1, wherein the position information of pixels corresponding the outline of the iris comprised in the eye and the position information of pixels corresponding the outline of the eye are obtained by segmentation model.

3. The computer-implemented method of predicting thyroid eye disease of claim 1, wherein the first processed image comprises a first processed left eye image and a first processed right eye image, and wherein the second processed image comprises a second processed left eye image and a second processed right eye image.

4. The computer-implemented method of predicting thyroid eye disease of claim 3, wherein the conjunctival hyperemia prediction model comprises a left eye conjunctival hyperemia prediction model and a right eye conjunctival hyperemia prediction model, wherein the conjunctival edema prediction model comprises a left eye conjunctival edema prediction model and a right eye conjunctival edema prediction model, wherein the lacrimal edema prediction model comprises a left eye lacrimal edema prediction model and a right eye lacrimal edema prediction model, wherein the eyelid redness prediction model comprises a left eye eyelid redness prediction model and a right eye eyelid redness prediction model, and wherein the eyelid edema prediction model comprises a left eye eyelid edema prediction model and a right eye eyelid edema prediction model.

5. The computer-implemented method of predicting thyroid eye disease of claim 4, wherein the predicted value for the conjunctival hyperemia is determined based on a result obtained by inputting the first processed left eye image to the left eye conjunctival hyperemia prediction model and a result obtained by inputting the first processed right eye image to the right eye conjunctival hyperemia prediction model, wherein the predicted value for the conjunctival edema is determined based on a result obtained by inputting the first processed left eye image to the left eye conjunctival edema prediction model and a result obtained by inputting the first processed right eye image to the right eye conjunctival edema prediction model, wherein the predicted value for the lacrimal edema is determined based on a result obtained by inputting the first processed left eye image to the left eye lacrimal edema prediction model and a result obtained by inputting the first processed right eye image to the right eye lacrimal edema prediction model, wherein the predicted value for the eyelid redness is determined based on a result obtained by inputting the second processed left eye image to the left eye eyelid redness prediction model and a result obtained by inputting the second processed right eye image to the right eye eyelid redness prediction model, and wherein the predicted value for the eyelid edema is determined based on a result obtained by inputting the second processed left eye image to the left eye eyelid edema prediction model and a result obtained by inputting the second processed right eye image to the right eye eyelid edema prediction model.

6. The computer-implemented method of predicting thyroid eye disease of claim 3, further comprises:

processing any one of the first processed left eye image and the first processed right eye image by inverting left and right, and processing any one of the second processed left eye image and the second processed right eye image by inverting left and right.

7. The computer-implemented method of predicting thyroid eye disease of claim 6, wherein the predicted value for the conjunctival hyperemia is determined based on results obtained by inputting the image laterally inverted and by inputting the image not laterally inverted to the conjunctival hyperemia prediction model, wherein the predicted value for the conjunctival edema is determined based on results obtained by inputting the image laterally inverted and by inputting the image not laterally inverted to the conjunctival edema prediction model, wherein the predicted value for the lacrimal edema is determined based on results obtained by inputting the image laterally inverted and by inputting the image not laterally inverted to the lacrimal edema prediction model, wherein the predicted value for the eyelid redness is determined based on results obtained by inputting the image laterally inverted and by inputting the image not laterally inverted to the eyelid redness prediction model, and wherein the predicted value for the eyelid edema is determined based on results obtained by inputting the image laterally inverted and by inputting the image not laterally inverted to the eyelid edema prediction model.

8. The computer-implemented method of predicting thyroid eye disease of claim 3, further comprises:

resizing the first processed left eye image and the first processed right eye image, and resizing the second processed left eye image and the second processed right eye image.

9. The computer-implemented method of predicting thyroid eye disease of claim 1, further comprises obtaining user responses with respect to a spontaneous retrobulbar pain and a pain on an attempted upward or downward gaze, and, wherein the determining the possibility comprises calculating a clinical activity score based on the predicted values for the conjunctival hyperemia, the conjunctival edema, the lacrimal edema, the eyelid redness, and the eyelid edema, and the obtained responses for the spontaneous retrobulbar pain and the pain on an attempted upward or downward gaze.

10. The computer-implemented method of predicting thyroid eye disease of claim 1, further comprises outputting information for recommending that a user visit a hospital in response to determining a clinical activity score is equal to or greater than a score of 3, wherein a score assigned to each symptom is a score of 1.

* * * * *